(12) United States Patent
Wood et al.

(10) Patent No.: US 12,098,354 B2
(45) Date of Patent: Sep. 24, 2024

(54) MICROPATTERNED HYDROGEL FOR CELL CULTURES

(71) Applicant: SOUTH DAKOTA BOARD OF REGENTS, Pierre, SD (US)

(72) Inventors: Scott Wood, Rapid City, SD (US); Ram Saraswat, Rapid City, SD (US)

(73) Assignee: SOUTH DAKOTA BOARD OF REGENTS, Pierre, SD (US)

( * ) Notice: Subject to any disclaimer, the term of this patent is extended or adjusted under 35 U.S.C. 154(b) by 943 days.

(21) Appl. No.: 16/838,511

(22) Filed: Apr. 2, 2020

(65) Prior Publication Data
US 2020/0318050 A1  Oct. 8, 2020

Related U.S. Application Data

(60) Provisional application No. 62/828,857, filed on Apr. 3, 2019.

(51) Int. Cl.
| | | |
|---|---|---|
| *C12N 5/077* | (2010.01) | |
| *C12M 1/00* | (2006.01) | |
| *C12M 1/12* | (2006.01) | |

(52) U.S. Cl.
CPC ............ *C12M 25/14* (2013.01); *C12M 23/20* (2013.01); *C12N 5/0655* (2013.01); *C12M 25/06* (2013.01); *C12N 2533/00* (2013.01); *C12N 2533/30* (2013.01); *C12N 2533/76* (2013.01); *C12N 2535/10* (2013.01)

(58) Field of Classification Search
None
See application file for complete search history.

(56) References Cited

U.S. PATENT DOCUMENTS

2013/0122580 A1\* 5/2013 Tsukada ................ C08J 7/0427
435/289.1

OTHER PUBLICATIONS

Formica et al. A Bioinspired Ultraporous Nanofiber-Hydrogel Mimic of the Cartilage Extracellular Matrix (2016), Advanced Healthcare Materials, 5, pp. 3129-3138. (Year: 2016).\*
Coburn et al. Bioinspired nanofibers support chondrogenesis for articular cartilage repair (2012), PNAS, 109, pp. 10012-10017. (Year: 2012).\*
Kolewe et al. Bacterial Adhesion Is Affected by the Thickness and Stiffness of Poly(ethylene glycol) Hydrogels, (2018), Applied Materials and Interfaces, 10, pp. 2275-2281. (Year: 2018).\*
Zhou et al. Restoration of chondrocytic phenotype on a two-dimensional micropatterned surface, (2015), Biointerphases, 10, pp. 1-10. (Year: 2015).\*
Tsai et al. Poly(dopamine) coating of scaffolds for articular cartilage tissue engineering, (2011), Acta Biomaterialia, 7, pp. 4187-4194. (Year: 2011).\*

Ahmed, Enas M., "Hydrogel: Preparation, characterization, and applications: A review", Journal of Advanced Research, vol. 6, pp. 105-121, 2015.
Andriacchi et al., "A Framework for the in Vivo Pathomechanics of Osteoarthritis at the Knee" Annals of Biomedical Engineering, vol. 32, No. 3, pp. 447-457, Mar. 2004.
Arzi et al., "Naturally occurring osteoarthritis in the domestic rabbit: possible implications for bioengineering research", Lab Anim., vol. 41(1), pp. 20-25, Feb. 12, 2015.
Ball, Vincent, "Polydopamine Nanomaterials: Recent Advances in Synthesis Methods and Applications", Frontiers in Bioengineering and Biotechnology, vol. 6, Article 109, 12 pages, Aug. 17, 2018.
Bendele, A.M., "Animal models of osteoarthritis", J Musculoskel Neuron Interact, vol. 1(4), pp. 363-376, Jan. 21, 2001.
Bendele et al., "Effects of Body Weight Restriction on the Development and Progression of Spontaneous Osteoarthritis in Guinea Pigs", Arthritis and Rheumatism, vol. 34, No. 9, pp. 1180-1184, Sep. 1991.
Benya et al., "Dedifferentiated Chondrocytes Reexpress the Differentiated Collagen Phenotype When Cultured in Agarose Gels", Cell., vol. 30, pp. 215-224, Aug. 1982.
Bijlsma et al., "Osteoarthritis: an update with relevance for clinical practice", Lancet, vol. 377, pp. 2115-2126, Jun. 18, 2011.
Boschetti et al., "Biomechanical properties of human articular cartilage under compressive loads", Biorheology, vol. 41, pp. 159-166, Feb. 2004.
Bradley et al., "Comparison of an Antiinflammatory Dose of Ibuprofen, an Analgesic Dose of Ibuprofen, and Acetaminophen in the Treatment of Patients with Osteoarthritis of the Knee", The New England Journal of Medicine, vol. 325, No. 2, pp. 87-91, Jul. 11, 1991.
Buschmann et al., "Chondrocytes in Agarose Culture Synthesize a Mechanically Functional Extracellular Matrix", Journal of Orthopaedic Research, vol. 10, pp. 745-758, Jun. 2, 1992.
Cook et al., "Instructional Review: Knee—Animal models of cartilage repair", Bone Joint Res., vol. 3, No. 4, pp. 89-94, Apr. 2014.
Cooke et al., "Geometric confinement is required for recovery and maintenance of chondrocyte phenotype in alginate", APL Bioengineering, vol. 1-016104, 13 pages, Oct. 9, 2017.
Cope et al., "Models of osteoarthritis: the good, the bad and the promising", Osteoarthritis and Cartilage, vol. 27, pp. 230-239, 2019.
Darling et al., "Mechanical properties and gene expression of chondrocytes on micropatterned substrates following dedifferentiation in monolayer", Cell. Mol. Bioeng., vol. 2(3), pp. 395-404, Aug. 9, 2009.
Darling et al., "Viscoelastic properties of zonal articular chondrocytes measured by atomic force microscopy", Osteoarthritis and Cartilage, vol. 14, pp. 571-579, 2006.

(Continued)

*Primary Examiner* — Kara D Johnson
*Assistant Examiner* — Maytee Marie Contes De Jesus
(74) *Attorney, Agent, or Firm* — McKee, Voorhees & Sease, PLC

(57) ABSTRACT

The present disclosure describes hydrogels which are micropatterned with a network of wells for cell culture. In a preferred embodiment, the micropatterned hydrogels are embedded with a nanomaterial. Further described are methods of forming the micropatterned hydrogels and methods of culturing cells in the micropatterned hydrogels. The hydrogels can be natural or synthetic.

18 Claims, 19 Drawing Sheets

(56) References Cited

OTHER PUBLICATIONS

Darling et al., "Spatial Mapping of the Biomechanical Properties of the Pericellular Matrix of Articular Cartilage Measured In Situ via Atomic Force Microscopy", Biophysical Journal, vol. 98, pp. 2848-2856, Jun. 2010.
Derendorf et al., "Pharmacokinetics and pharmacodynamics of glucocorticoid suspensions after intra-articular administration", Clin. Pharmacol Ther., vol. 39, No. 3, pp. 313-317, Mar. 1986.
Destaye et al., "Glutaraldehyde Vapor Cross-linked Nanofibrous PVA Mat with in Situ Formed Silver Nanoparticles", Applied Materials & Interfaces, Research Article, 8 pages, May 13, 2013.
Dibartola et al., "Correlation between histological outcome and surgical cartilage repair technique in the knee: A meta-analysis", The Knee, vol. 23, pp. 344-349, Jan. 17, 2016.
Duarte Campos et al., "Supporting Biomaterials for Articular Cartilage Repair", Cartilage, vol. 3(3), pp. 205-221, 2012.
Duraine et al., "Emergence of Scaffold-free Approaches for Tissue Engineering Musculoskeletal Cartilages", Ann. Biomed Eng., vol. 43(3), pp. 543-554, Mar. 2015.
Fang et al., "Three-Dimensional Cell Cultures in Drug Discovery and Development", SLAS Discovery, vol. 22(5), pp. 456-472, Jan. 30, 2017.
Ferdowsian et al., "Sings of Mood and Anxiety Disorders in Chimpanzees", PLoS One, vol. 6, Issue 6, 11 pages, Jun. 2011.
Ghetie et al., "Drying of Agarose Gel Beads", Specialia, pp. 1384-1385, Dec. 15, 1971.
Glowacki et al., "Cell Shape and Phenotypic Expression in Chondrocytes (41533)", Proceedings of the Society for Experimental Biology and Medicine, vol. 172, pp. 93-98, 1983.
Gregory et al., "A Review of Translational Animal Models for Knee Osteoarthritis", Arthritis, vol. 2012, Article ID 764621, 14 pages, Nov. 26, 2012.
Grimshaw et al., "Bovine articular chondrocyte function in vitro depends upon oxygen tension", Osteoarthritis and Cartilage, vol. 8, No. 5, pp. 386-392, 2000.
Han et al., "Mussel-inspired tissue adhesive hydrogel based on polydopamine-chondroitin sulfate complex for growth-factor-free cartilage regeneration", Applied Materials & Interfaces, http://pubs.acs.org, 49 pages, Jul. 27, 2018.
Hargrave-Thomas et al., "The bovine patella as a model of early osteoarthritis", J. Anat., vol. 223, pp. 651-664, Aug. 29, 2013.
Harvey et al., "Facile synthesis of ultrasmall polydopamine-polyethylene glycol nanoparticles for cellular delivery", Biointerphases, vol. 13(6), 11 pages, Nov. 2018.
Hassan et al., "Structure and Morphology of Freeze/Thawed PVA Hydrogels", Macromolecules, vol. 33, pp. 2472-2479, 2000.
Hu et al., "Chemically cross-linked chitosan hydrogel loaded with gelatin for chondrocyte encapsulation", Biotechnology Journal, vol. 6, pp. 1388-1396, Jun. 12, 2011.
Hutter et al., "Calibration of atomic-force microscope tips", Rev. Sci. Instrum., vol. 64(7), pp. 1868-1873, Apr. 12, 1993.
Hynd et al., "Directed cell growth on protein-functionalized hydrogel surfaces", J. Neurosei. Methods, vol. 162(1-2), pp. 255-263, May 15, 2007.
Jiang et al., "PVA hydrogel properties for biomedical application", Journal of the Mechanical Behavior of Biomedical Materials, vol. 4, pp. 1228-1233, Apr. 6, 2011.
Kavanaugh et al., "Particle Based Technologies for Osteoarthritis Detection and Therapy", Drug Deliv. Transl. Res., vol. 6(2), pp. 132-147, Apr. 2016.
Kim et al., "A practical guide to microfluidic perfusion culture of adherent mammalian cells", Lab on a Chip, vol. 7, pp. 681-694, Apr. 16, 2007.
Kirwan, M.D., John R., "The Effect of Glucocorticoids on Joint Destruction in Rheumatoid Arthritis", The New England Journal of Medicine, vol. 333, No. 3, pp. 142-146, Jul. 20, 1995.
Kirwan et al., "Intra-articular therapy in osteoarthritis", Bailliere's Clinical Rheumatology, vol. 11, No. 4, pp. 769-794 Nov. 1997.
Kudo et al., "Structural changes of water in poly(vinal alcohol) hydrogel during dehydration", The Journal of Chemical Physics, vol. 140, 8 pages, Jan. 10, 2014.
Kuyinu et al., "Animal models of osteoarthritis: classification, update, and measurement of outcomes", Journal of Orthopaedic Surgery and Research, vol. 11:19, 27 pages, 2016.
Lawrence et al., "Estimates of the Prevalence of Arthritis and Other Rheumatic Conditions in the United States", Arthritis & Rheumatism, vol. 58, No. 1, pp. 26-35, Jan. 2008.
Lee et al., "A Current Review of Molecular Mechanisms Regarding Osteoarthritis and Pain", Gene, vol. 527(2), pp. 440-447, Sep. 25, 2013.
Lee et al., "Clinical translation of stem cells: insight for cartilage therapies", Crit. Rev. Biotechnol., vol. 34(1), pp. 89-100, Mar. 2014.
Loeser, Richard F., "Integrin-Mediated Attachment of Articular Chondrocytes to Extracellular Matrix Proteins", Arthritis and Rheumatism, vol. 36, No. 8, pp. 1103-1110, Aug. 1993.
Mayne et al., "Changes in type of collagen synthesized as clones of chick chondrocytes grow and eventually lose division capacity", Proc. Natl. Acad. Sci., vol. 73, No. 5, pp. 1674-1678, May 1976.
McCoy, A.M., "Animal Models of Osteoarthritis: Comparisons and Key Considerations", Veterinary Pathology, vol. 52 (5), pp. 803-818, 2015.
Mishra et al., "Synthesis and Characterization of Electrospun Nanocomposite $TiO_2$ Nanofibers with Ag Nanoparticles for Photocatalysis Applications", Journal of Nanomaterials, vol. 2012, Article ID 902491, 6 pgs, Nov. 2011.
Nebelung et al., "Functional in situ assessment of human articular cartilage using MRI: a whole-knee joint loading device", Biomech. Model Mechanobiol., 16 pages, Jun. 23, 2017.
Niederauer et al., "Correlation of Cartilage Stiffness to Thickness and Level of Degeneration Using a Handheld Indentation Probe", Annals of Biomedical Engineering, vol. 32, No. 3, pp. 352-359, Mar. 2004.
O'Connell et al., "Toward Engineering a Biological Joint Replacement", J. Knee Surg., vol. 25(3), pp. 187-196, Jul. 2012.
Pauly et al., "Mechanical Properties and Cell Compatibility of Agarose Hydrogels Containing Proteoglycan Mimetic Graft Copolymers", BioMacromolecules, http://pubs.acs.org, 46 pages, Jun. 17, 2017.
Pedersen et al., "Comparative digital cartilage histology for human and common osteoarthritis models", Orthop. Res. Rev., vol. 5, pp. 13-20, 2013.
Poole et al., "Recommendations for the use of preclinical models in the study and treatment of osteoarthritis", Osteoarthritis and Cariliage, vol. 18, pp. 510-516, May 11, 2010.
Priest et al., "Micro-patterned agarose gel devices for single-cell high-throughput microscopy of *E. coli* cells", www.nature/scientificreports, 7 pages, published online Dec. 21, 2017.
Proffen et al., "A Comparative Anatomical Study of the Human Knee and Six Animal Species", Knee, vol. 19(4), pp. 493-499, Aug. 2012.
Rosenzweig et al., "Culture of Primary Bovine Chondrocytes on a Continuously Expanding Surface Inhibits Dedifferentiation", Tissue Engineering: Part A, vol. 18, Nos. 23 & 24, pp. 2466-2476, 2012.
Salerno et al., "AFM Measurement of the Stiffness of Layers of Agarose Gel Patterned With Polylysine", Microscopy Research and Technique, vol. 73, pp. 982-990, Jan. 18, 2010.
Silberberg et al., "Age Changes of Bones and Joints in Various Strains of Mice", Developmental Dynamics, vol. 68, Issue 1, pp. 69-95, Jan. 1941.
Surrao et al., "Can Microcarrier-Expanded Chondrocytes Synthesize Cartilaginous Tissue In Vitro?", Tissue Engineering: Part A, vol. 17, Nos. 15 & 16, pp. 1959-1967, 2011.
Teeple et al., "Animal Models of Osteoarthritis: Challenges of Model Selection and Analysis", The AAPS Journal, vol. 15, No. 2, pp. 438-446, Apr. 2013.
Tsai et al., "Poly(dopamine) coating of scaffolds for articular cartilage tissue engineering", Acta Biomaterialia, vol. 7, pp. 4187-4194, Jul. 25, 2011.

(56) References Cited

OTHER PUBLICATIONS

Uchio et al., "Arthroscopic assessment of human cartilage stiffness of the femoral condyles and the patella with a new tactile sensor", Medical Engineering & Physics, vol. 24, pp. 431-435, Mar. 14, 2002.
Walters et al., "Short cantilevers for atomic force microscopy", Rev. Sci. Instrum., vol. 67(10), pp. 3583-3590, Oct. 1996.
Whitesides et al., "Soft Lithography in Biology and Biochemistry", Annu. Rev. Biomed. Eng., vol. 3, pp. 335-373, 2001.
Williams et al., "A Novel Family of Cyclic Peptide Antagonists Suggests that N-cadherin Specificity is Determined by Amino Acids that Flank the HAV Motif", Journal of Biological Chemistry, vol. 275, No. 6, pp. 4007-4012, Feb. 11, 2000.
Williams et al., "INP, a Novel N-cadherin Antagonist Targeted to the Amino Acids that Flank the HAV Motif", Molecular and Cellular Neuroscience, vol. 15, pp. 456-464, 2000.
Wood et al., "Cysteine-Mediated Redox Regulation of Cell Signaling in Chondrocytes Stimulated with Fibronectin Fragments", Arthritis & Rheumatology, vol. 68, No. 1, pp. 117-126, Jan. 2016.
Yu et al., "Mussel-Inspired Adhesive Polydopamine-Functionalized Hyaluronic Acid Hydrogel with Potential Bacterial Inhibition", Global Challenges, vol. 4, 7 pages, 2020.
Zhou et al., "Restoration of chondrocytic phenotype on a two-dimensional micropatterned surface", BioInterphases, vol. 10(1), 9 pages, Mar. 2015.
Zhu et al., "Optimization of Glutaraldehyde Vapor Treatment for Electrospun Collagin/Silk Tissue Engineering Scaffolds", ACS Omega, vol. 2, pp. 2439-2450, Jun. 2, 2017.

\* cited by examiner

Top View

Side View

Lithographic Features

CellWell

Crosslinked PVA nanofibers

Ankle Collagen II nanofibers

MICROPATTERNED HYDROGEL FOR CELL CULTURES

CROSS-REFERENCE

This application is related to and claims priority under 35 U.S.C. § 119 to U.S. Provisional Application Ser. No. 62/828,857 filed on Apr. 3, 2019 and entitled "MICROPATTERNED HYDROGEL FOR CELL CULTURES"; the entire contents of this patent application are hereby expressly incorporated herein by reference.

TECHNICAL FIELD

The present disclosure relates to micropatterned hydrogels. Preferably, the hydrogels are micropatterned with a plurality of wells for cell cultures.

BACKGROUND

Osteoarthritis (OA) is a painful disease of the articular joints that is primarily characterized by the degradation of the extracellular matrix (ECM) in the articular cartilage. To date, surgical restoration techniques used for cartilage repair do not regenerate hyaline articular cartilage. Although symptoms can improve temporarily after surgical repair, 85% of patients progress to failure within 7.5 years or less. There are currently no known medical treatments that effectively address the underlying molecular causes of OA. Articular chondrocytes are the only cells in the articular cartilage and are responsible for the maintenance of cartilage homeostasis between digestion and replacement of old or damaged tissue components. It is well-accepted that a loss of this homeostatic balance is responsible for the development of OA. Current pharmaceutical treatment options are limited to the use of analgesics like non-steroidal anti-inflammatory drugs (NSAID) and intra-articular corticosteroid injections to reduce the pain associated with inflammation, which only provides temporary relief and can have negative consequences with long-term use.

Animal models have long been the gold standard for understanding the progression of OA. However, they are also associated with concerns of ethical issues regarding the treatment of animals, cost and management issues, anatomical differences of cartilage in animals compared to humans, and age variations of animal species at the time of testing.

Due to the problems associated with animal models, chondrocytes have been studied in vitro using either standard two-dimensional (2D) or any number of three-dimensional (3D) cell culture techniques. Two-dimensional (2D) cell culture techniques are particularly unsuitable for articular chondrocytes. In vivo, articular chondrocyte morphology is generally spheroidal throughout most of the cartilage, and this spheroidal morphology is widely considered to be the canonical morphology of chondrocytes for in vitro studies. Under standard 2D culture conditions, however, chondrocytes tend to develop an artificially-induced fibroblastic phenotype after expansion or more than approximately 10 days in culture, which is known to alter their behavior.

Three-dimensional (3D) scaffolds have shown promise for promotion of phenotype maintenance of articular chondrocytes and for chondrogenesis of mesenchymal stem cells (MSCs), however, although the past decade has realized significant progress in the development of many types of three-dimensional (3D) cell culture systems, these techniques are all inherently limited in their utility by restricted oxygen diffusion, restricted and non-uniform penetration of both small molecule and macromolecule treatment agents, and limited optical penetration depth.

There remains a paucity of such systems that are well-suited for high-resolution optical imaging of large numbers of adherent cells (e.g., using high-throughput techniques). There is, therefore, a vital need for a culture model that combines the physiological advantages of 3D cell culture with the practical advantages of 2D culture to enable advances in the understanding of osteoarthritis pathogenesis with sufficient translational potential that more effective treatments may be developed.

SUMMARY OF THE INVENTION

In an aspect, the composition of the present application comprises a hydrogel, wherein the hydrogel is micropatterned with a plurality of wells. In a further aspect, the hydrogel is biocompatible, and may be natural and/or synthetic. In an aspect, the hydrogel further comprises nanofibers embedded within the hydrogel. In an embodiment, the nanofibers are biocompatible. In some aspects of the application, the nanofibers are synthetic and/or natural. Additionally, in an embodiment, the nanofibers are composite nanofibers. The nanofibers may comprise, without limitation, polyvinyl alcohol, collagen, chitin, or a combination thereof. In an embodiment, the hydrogel includes, for example, agarose or polydimethyl siloxane. In some aspects the hydrogel is biphasic and/or multiphasic in the sense that the hydrogel incorporates components in multiple phases (e.g. solid, liquid, etc.), and/or that the hydrogel incorporates components having multiple morphologies, including without limitation components in differing shapes (e.g. hemispheroidal and/or non-hemispheroidal) and/or different arrangements (e.g. uniform arrangement/distribution or non-uniform arrangement/distribution), and/or that the hydrogel incorporates components comprised of different materials (e.g. agarose and PVC).

In an aspect, the plurality of wells in the hydrogel have an average diameter of between about 5 µm and about 50 µm. In a further aspect, the plurality of wells has an average diameter of between about 5 µm and about 30 µm. According to an embodiment, the plurality of wells are separated by an inter-well spacing of at least about 0.1 µm. In an embodiment, the inter-well spacing is between about 0.1 to about 100 µm, and in a further embodiment, the inter-well spacing is at least about 0.5 µm.

In an embodiment of the application, the hydrogel is on a substrate. According to an embodiment, the distance between the substrate and the plurality of wells is at least about 5 µm. In some aspects, the distance between the substrate and the plurality of wells is less than about 100 µm.

In an embodiment, the plurality of wells is unseeded with cells. In a further embodiment, the plurality of wells is seeded with cells. In an aspect of the invention, the composition has a cell seeding density of at least about 75,000 cells/cm$^2$, a cell seeding density of at least about 150,000 cells/cm$^2$, or a cell seeding density of at least about 275,000 cells/cm$^2$.

In some aspects, the plurality of wells is hemispheroidal in shape. In an aspect, the wells comprise the same shape. In an embodiment, the plurality of wells is not hemispheroidal in shape. In an embodiment, the plurality of wells is in an irregular shape, and/or comprise different shapes.

In an embodiment, the cells comprise one or more of a chondrocyte cell, a stem cell, an adipose cell, an immune cell, and/or any other desired type of cell. In an embodiment, the cells are spheroidal in shape. In a further embodiment, the cells are not spheroidal in shape. In some aspects, the cells may be of the same or different cell types, such that the cells are comprised of one or more cell types. In some aspects, the cells may be in a uniform arrangement or a non-uniform arrangement. In a further aspect, the cells may be arranged in reference to a structure, such as a scaffold. In an aspect, the cells need not utilize a scaffold. In a still further aspect, the cells may be arranged in order to the spacing and arrangement of the cell type's tissue.

In some aspects, the plurality of wells comprises a functionalized surface. In an aspect, the functionalized surface is functionalized to target a particular cell type to adhere to a substrate to promote adhesion to the substrates for at least about 3 days. In an embodiment, the cells maintain adherence for at least about 28 days. The functionalization procedure utilizes polydopamine (PDA) surface chemistry which facilitates the cells to adhere to the substrate.

The present application also provides for methods of forming the compositions described herein. In an aspect, the method of forming a composition according to the application comprises obtaining a hydrogel; and stamping the hydrogel to form a plurality of wells. In an aspect, the method further comprises the step of forming the hydrogel.

In an embodiment, the hydrogel is biodegradable. In a further embodiment, hydrogel includes, without limitation, agarose or polydimethyl siloxane.

In an aspect, the method further comprises mixing the hydrogel with nanomaterials before stamping. In an embodiment, the nanomaterials comprise nanofibers and/or nanoparticles. In a further embodiment, the nanomaterials include, without limitation, polyvinyl alcohol, collagen, chitin, or a combination thereof.

In an aspect, the stamping forms a plurality of hemispheroidal wells.

In some aspects, the method further comprises functionalizing the surface of the plurality of wells. In an embodiment, the surface of the plurality of wells is functionalized to target a particular cell type. In another embodiment, the plurality of wells comprises a polydopamine-based surface functionalization.

The present application also provides for methods of culturing cells. In an aspect, the methods comprise providing a composition as described herein and seeding the plurality of wells with at least one cell per well. In an embodiment, the plurality of wells is seeded with cells at a cell seeding density of at least about 75,000 cells/cm$^2$, at least about 150,000 cells/cm$^2$, or at least about 275,000 cells/cm$^2$.

In an aspect, the plurality of wells comprises a polydopamine-based surface functionalization. In an embodiment, the cells maintain adherence to the plurality of wells for at least about 28 days.

In some aspects, the application provides methods of preparing a device for stamping the hydrogel. In an embodiment, the method of preparing the stamping device comprises the steps as described substantially herein.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 2A shows primary human articular chondrocytes were found to have a mean diameter of 14.6±2.1 µm (S.D.) in suspension, with average diameters on a per-donor basis ranging from ~11-19 µm. FIG. 2B is a cell counter screenshot screen showing a representative single-donor chondrocyte diameter distribution.

FIG. 3A shows a representative section of photomask design. Units are in µm. FIG. 3B shows a cross-sectional representation of CellWell along the dashed line in FIG. 3A.

FIG. 4A is an Scanning Electron Microscopy (SEM) image of lithographic patterns used to create CellWells. FIG. 4B is a Phase Contrast Image of CellWell with three sizes of wells precisely sized to fit individual articular chondrocytes; Scale bars 10 µm. FIG. 4C shows optical profilometry cross-sectional profiles of individual wells (mean±S.D. of n=10 wells each). FIG. 4D shows macro-appearance of the CellWell; Scale bar 5 mm.

FIG. 5A shows Nanoindentation Phase. FIG. 5B shows Stress Relaxation Phase.

FIG. 6A shows Average Nanoindentation Curves of Agarose CellWells. FIG. 6B shows Average Stress Relaxation of Agarose CellWells and Articular Cartilage. FIG. 6C shows Average Nanoindentation Curves of Articular Cartilage. FIG. 6D shows Average Nanoindentation on Agarose CellWells at different strain rates.

FIG. 9A shows TEM images of PVA nanofibers post-crosslinking, and collagen II fibers, extracted from the ankle; scale bars 1 µm. FIG. 9B shows the distribution of crosslinked PVA nanofibers to recapitulate nature of the collagen II fibers of the extracellular matrix of articular cartilage within our CellWell articular cartilage model for isolated chondrocyte cell culture. Fiber measurements were obtained from n=3 independent samples, with individual measurements represented on the graph. FIG. 9C shows the anisotropic distribution (left) and isotropic distribution (right) of nanofibers embedded in agarose CellWell, Scale Bar: 50 μm.

FIG. 13A is a phase-contrast image of chondrocytes seeded for 4 weeks in a CellWell show robust maintenance of canonical spheroidal morphology, Scale Bar 50 μm. FIG. 13B shows macroscopic appearance of PDA-functionalized CellWell shows substantial darkening of the agarose. FIG. 13C shows aspect ratio measurements (mean±S.D., n=150 cells) over a period of 4 weeks show strong long-term maintenance of spheroidal morphology by the CellWell (p<0.0001 relative to 2D coverglass at each time point based on Kruskal-Wallis test with Dunn's multiple comparison post-hoc analysis).

DETAILED DESCRIPTION OF THE PREFERRED EMBODIMENTS

Figure 1:
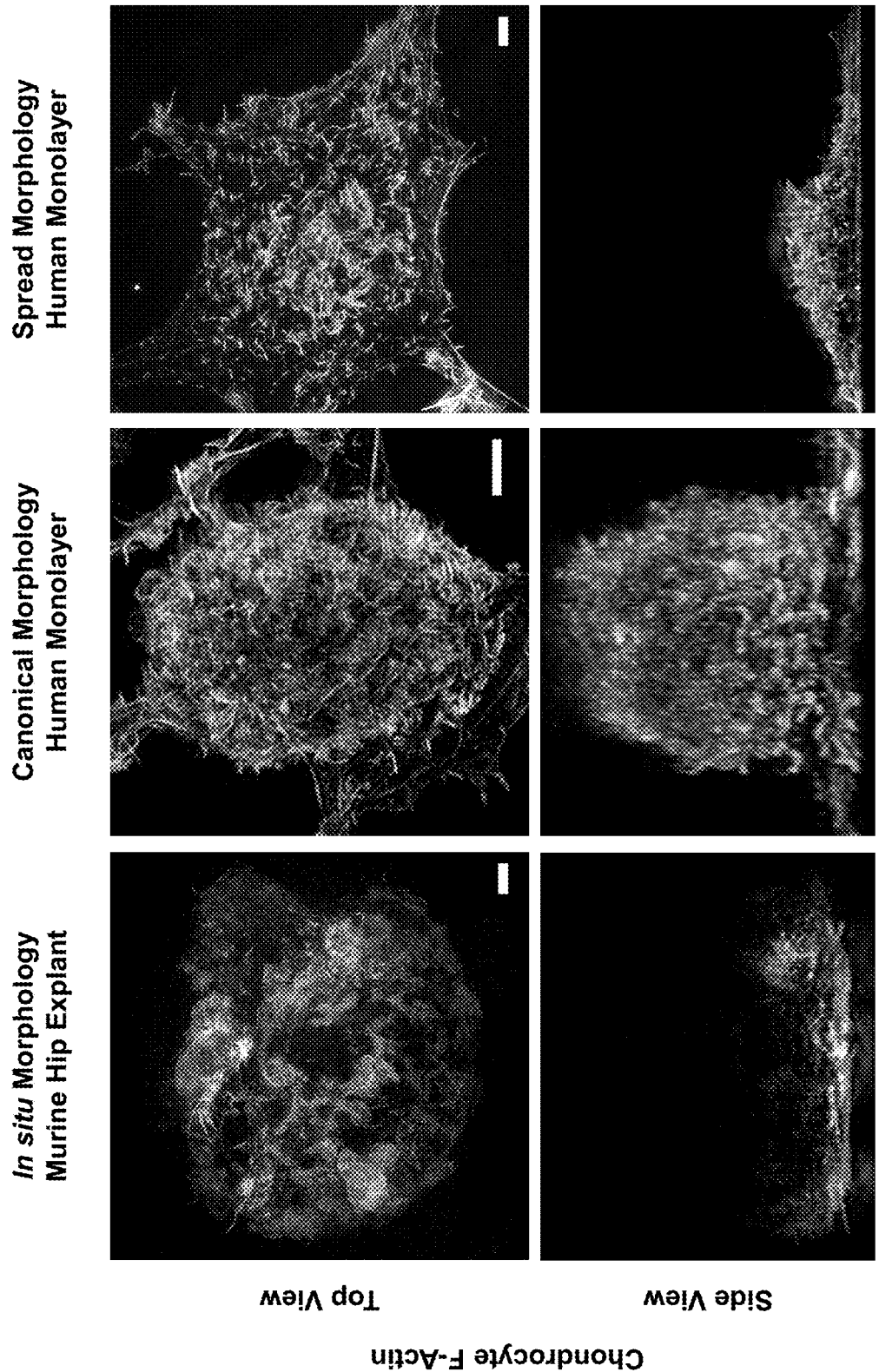
FIG. 1 shows chondrocyte morphology influences internal architecture. Murine femoral cap hip explants and primary human articular chondrocytes were plated on fibronectin-coated coverglass using standard 2D cell culture techniques, fixed with 4% paraformaldehyde, stained with ActinRed 555 Ready Probes® Reagent (ThermoFisher) and imaged in super-resolution using 3D structured illumination microscopy (3D-SIM) on a GE DeltaScan™ OMX SR microscope. Maximum intensity projections of volumetric image stacks are shown. Note in the side view of the murine hip explant that the turbidity of the tissue prevented imaging of all but the surface-most structures in the explant images, a common problem in imaging of both natural tissues and 3D cell cultures. Scale bars are 2 µm and apply to both top and side projections.

The present application addresses the deficiencies and needs described above in the background. Further, the present application may have further applications in the culture of other cell types, including the stem cell market, where it may help those cells to maintain their stemness during expansion and culture prior to experimentation.

Beneficially, the present application provides compositions for methods of producing wells suitable for seeding with at least one cell of a desired cell type, wherein the environment and patterning of the wells is physiologically representative of and/or mimics the spacing and arrangement of the cell type's tissue, and the spacing between the cells is small enough so as to allow communications with nearby cells.

More particularly, the present application has surprisingly found that it is possible to use adhesive thin films (e.g., packing tape) to regulate thickness of the device at 15 μm rather than having to use a much more complex lithographic approach.

Further, the present application has identified a way to manufacture the device of the present application using techniques for producing micro-lens arrays leading to well patterns to ensure it was energetically favorable for the cells to go in a preferred direction. Other challenges overcome by the present application include electrospinning fibers of appropriate diameter to match ankle cartilage type II collagen fibers, crosslinking fibers using vapor deposition of glutaraldehyde to prevent them from dissolving in the aqueous environment required for cell culture, and embedding fibers within agarose. In addition, the present application can align fibers, identify workable materials, (e.g., those that cure slowly enough to pattern), and prevent anoikis (massive cell death due to lack of adhesion) during seeding.

In addition to the aforementioned uses, the present application further provides methods of functionalizing well surfaces, for example by using covalent crosslinking methods to adhere extracellular matrix (ECM) proteins to well surfaces. In an aspect, a wide variety of physiologically relevant materials may be incorporated into the hydrogel or used to functionalize well surfaces, including, without limitation, hyaluronic acid-, chondroitin sulfate-, collagen II-derived materials, or polydopamine (PDA). In a preferred embodiment, the well surface is functionalized with polydopamine. In a preferred embodiment, the compositions comprise a natural hydrogel and well surface functionalization with PDA agarose. In a most preferred embodiment, the compositions comprise an agarose hydrogel and well surface functionalized with PDA. In addition to incorporating physiologically relevant materials into the hydrogel, the well design may beneficially be varied to incorporate more physiologically representative distributions of well geometries and spacings, and nanomaterial arrangement. Such varied geometry and spacings may include, without limitation, an arrangement mimicking/creating cell pairing, discoid geometries, triangular geometries, etc. With respect to articular chondrocyte cells specifically, the well geometries, spacings, and materials may be configured to model (either independently or in co-culture) the three zones of articular cartilage (superficial zone, middle zone, deep zone), in both well geometry and nanomaterial arrangement. Beyond articular chondrocyte cells, the hydrogels and methods of making as described herein may apply to any cell type, including without limitation, stem cells, adipose cells, immune cells, and others.

Chondrocytes maintain their spheroidal morphology over at least about 28 days. The expression levels of phenotypic marker proteins collagen II, aggrecan, Sox-9 (SRY-Box Transcription Factor 9), and decorin in chondrocytes seeded in a CellWell will be at least about 50% greater than for chondrocytes seeded in monolayer on tissue culture-treated polystyrene culture dishes. The expression levels of de-differentiation marker proteins Collagen I, Collagen X, and Ki-67 will be at least 50% lower than for chondrocytes seeded in monolayer on tissue culture-treated polystyrene culture dishes.

The embodiments of this invention are not limited to the particular embodiments illustrated as examples herein, which can vary. Other objects, advantages and features of the present invention will become apparent from the following description taken in conjunction with the accompanying drawings.

Definitions

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation. The preferred materials and methods are described herein. In describing and claiming the embodiments of the present invention, the following terminology will be used in accordance with the definitions set out below.

For example, as used in this specification and the appended claims, the singular forms "a," "an" and "the" can include plural referents unless the content clearly indicates otherwise. Further, all units, prefixes, and symbols may be denoted in its SI accepted form. Numeric ranges recited within the specification are inclusive of the numbers defining the range and include each integer within the defined range.

Numeric ranges recited within the specification are inclusive of the numbers defining the range and include each integer within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾ This applies regardless of the breadth of the range.

The term "about," as used herein, refers to variation in the numerical quantity that can occur, for example, through typical measuring techniques and equipment, with respect to any quantifiable variable, including, but not limited to, mass, volume, time, temperature, length, density, etc. Further, given typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about," the claims include equivalents to the quantities.

The term "actives" or "percent actives" or "percent by weight actives" or "actives concentration" are used interchangeably herein and refers to the concentration of those ingredients involved in cleaning expressed as a percentage minus inert ingredients such as water or salts.

The term "weight percent," "wt. %," "wt-%," "percent by weight," "% by weight," and variations thereof, as used herein, refer to the concentration of a substance as the weight of that substance divided by the total weight of the composition and multiplied by 100.

A "hydrogel" as used herein refers to a polymeric material which exhibits the ability to swell in water and to retain a significant portion of water within its structure without dissolution. Hydrogels are typically three-dimensional macromolecular networks in water formed from a cross-linked polymer.

The term "nanofiber" as used herein refers to fibers with diameters smaller than of 1.0 micrometer, and generally between 10 nanometers and 1.0 micrometer, such as between 200 nm and 600 nm.

The term "composite nanofibers" as used herein are nanofibers produced from at least two different polymers.

Micropatterned Hydrogels

This disclosure relates to hydrogels micropatterned with wells. In a preferred embodiment, the micropatterned hydrogels are nanocomposites, in that they include one or more types of nanomaterials, wherein the nanomaterials may include nanofibers and/or nanoparticles. Preferably, the micropatterned hydrogels can serve as a platform for cell cultures with a plurality of wells that are sized to fit individual cells so that the wells can hold cells. The hydrogel can be on a substrate. Any suitable substrate can be used including, but not limited to, glass, metal, composite, or a combination thereof. Preferably, the wells are raised above the underlying substrate by about 100 μm or less to facilitate high resolution fluorescence imaging on an inverted microscope while still maintaining physical separation between the cells and the underlying substrate. The hydrogel can be prepared with or without nanomaterials, such as nanofibers and/or nanoparticles, embedded within it. It should be understood that the hydrogel need not comprise nanomaterials.

Hydrogels and nanofibers useful in the invention can be derived from natural materials or synthetic materials. Representative natural polymers include, but are not limited to, alginate, collagen, chitosan, dextran, gelatin, cellulose, agarose, pectin, starch, gellan, hyaluronic acid, xanthan, and agaropectin. Representative synthetic polymers include, but are not limited to, poly(hydroxy acids) such as poly(lactic acid), poly(glycolic acid), and poly(lactic acid-co-glycolic acid), poly(lactide), poly(glycolide), poly(lactide-co-glycolide), polyanhydrides, polyorthoesters, polyamides, polycarbonates, polyalkylenes such as polyethylene and polypropylene, polyalkylene glycols such as poly(ethylene glycol), polyalkylene oxides such as poly(ethylene oxide), polyalkylene terepthalates such as poly(ethylene terephthalate), polyvinyl alcohols, polyvinyl ethers, polyvinyl esters, polyvinyl halides such as poly(vinyl chloride), polyvinylpyrrolidone, polysiloxanes, poly(vinyl alcohols), poly(vinyl acetate), polystyrene, polyurethanes and co-polymers thereof, derivatized celluloses such as alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulfate sodium salt, polymers of acrylic acid, methacrylic acid or copolymers or derivatives thereof including esters, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate), poly(butyric acid), poly(valeric acid), and poly(lactide-co-caprolactone), copolymers and blends thereof.

Preferably the hydrogel comprises a biodegradable hydrogel biomaterial to mimic the proteoglycans of the native articular cartilage extracellular matrix. In a preferred embodiment, the hydrogel is embedded with non-biodegradable nanomaterials such as nanofibers and/or nanoparticles to mimic the type II collagen network of articular cartilage. This model is generated using electrospinning and soft contact lithography techniques. A wide variety of materials can be used for each component. A preferred embodiment comprises agarose hydrogels embedded with poly(vinyl alcohol) nanofibers due to their balance of optical, mechanical, and biological properties with ease of use.

An advantage of the micropatterned hydrogels is the relatively minimal distance between wells. In some embodiments, the plurality of wells is separated by a fixed distance between any two consecutive wells. In another embodiment, the plurality of wells is separated by a range of distances between consecutive wells. This provides cells with the flexibility to either directly contact their neighboring cells by reaching over the space between wells or to remain in isolation. This flexibility provides immense possibilities for researchers interested in understanding the effects of cell-cell contact mechanics. In an exemplary embodiment, the micropatterned hydrogel provides a range of distances between consecutive wells ranging from a minimal distance of about 2.5 µm (slightly larger than the separation between cell pairs within chondrons in vivo) to a maximum distance of about 15 µm.

In some embodiments, the wells of the micropatterned hydrogel have fixed well diameters. In another embodiment, the wells of the micropatterned hydrogel have variable well diameters. Chondrocytes, like most cells, have a wide range of sizes. By providing a platform with a representative distribution of well diameters, the hydrogel can provide a more natural environment for any given cell than systems with single fixed diameters.

EXAMPLES

In these examples, we establish the proof of concept for a unique micropatterned nanocomposite cell culture platform, the CellWell, which consists of a thin film micropatterned nanofiber-embedded hydrogel substrate that fits a single cell within each well and facilitates high throughput fluorescence imaging of chondrocytes. The substrate composition was chosen to recapitulate the ECM of articular cartilage wherein a hydrogel models cartilage proteoglycans and embedded nanofibers model collagen II fibers. Goals for the design of the CellWell included: (1) designing the wells such that their geometries reinforce the canonical spheroidal chondrocyte morphology for each cell; (2) matching the mechanical stiffness of articular cartilage ECM or the chondrocyte pericellular matrix (PCM) as closely as possible; (3) matching the diameters of the embedded nanofiber diameters as closely as possible to those of the native collagen II fibers; and (4) ensuring compatibility with traditional cell culture and live-cell imaging techniques.

Example 1: Chondrocyte Morphology Influences Internal Architecture

When plated on standard 2D platforms, chondrocytes tend to rapidly lose their canonical spheroidal morphology due to the adherent chondrocyte cells being on a hard and flat substrate, and adopt a fibroblastic phenotype within 10-14 days of culture. These morphological changes can result in substantial changes to chondrocyte architecture, including the length, density, and distribution of cortical actin fibers. The in situ chondrocyte shown in FIG. 1 (left) can be seen to have an actin network with length and density more similar to the chondrocyte displaying the canonical phenotype in FIG. 1 (middle), than to that of the chondrocyte in FIG. 1 (right) which has a spread morphology that is more typical of chondrocytes in standard monolayer culture. Note that the in situ chondrocyte in FIG. 1 (lower left) is not flat, but that the turbidity of the tissue prevented imaging its full thickness, thereby illustrating the difficulties inherent to imaging cells in 3D samples. It has long been known that forcing chondrocytes to adopt a rounded morphology leads to enhancement of a chondrocyte phenotype in vitro; however, the techniques utilized previously have all relied upon restriction of binding area on a 2D substrate to prevent spreading rather than active promotion of a rounded phenotype in a way that does not inherently limit adhesion.

Example 2: Chondrocyte Diameter

Figure 2A:
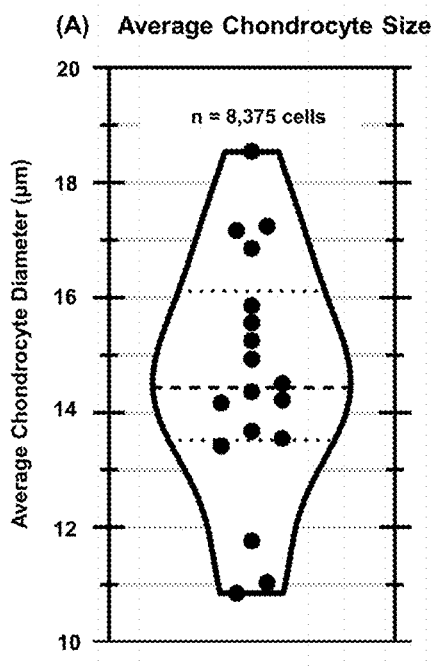
FIGS. 2A-B depict chondrocyte diameter distribution.
Figure 2B:
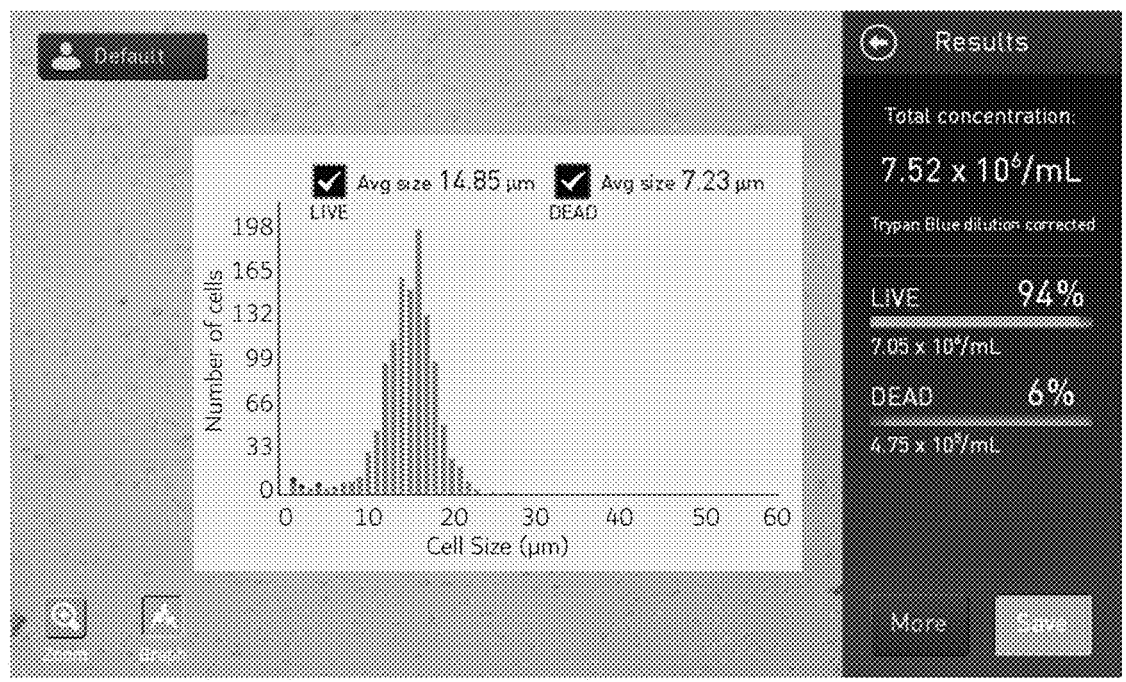

The diameter of 8,375 chondrocytes from 18 independent donors was measured using a Countless II FL cell counter. As shown in FIG. 2A, human chondrocytes were found to have a mean diameter of 14.6 µm±2.1 µm (S.D.), and this data represented the diameter measurements from 8,375 cells over n=18 individual donors. For each donor, the cell counter provided direct measurements of cell density (i.e., number), viability (based on trypan blue exclusion, circularity, and diameter), and average diameter, as well as a pictographic histogram of the distribution of diameters within the sample. The chondrocyte diameter distribution of average donors depicted a Full Width at Half Maxima (FWHM) of 12-18 µm, as shown in FIG. 2B. These measurements served as the basis for the selection of CellWell diameters of 12, 15, and 18 µm.

Example 3: CellWell Design and Manufacturing

Figure 3A:
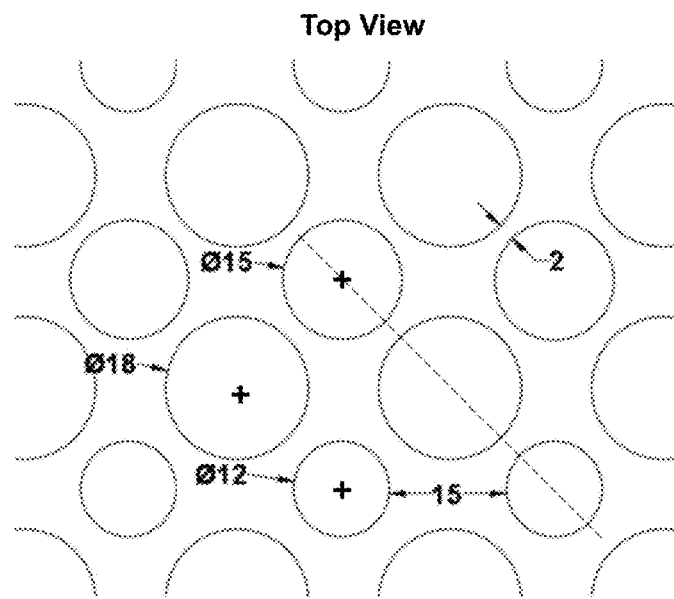
FIGS. 3A-B show CellWell design schematics.
Figure 3B:
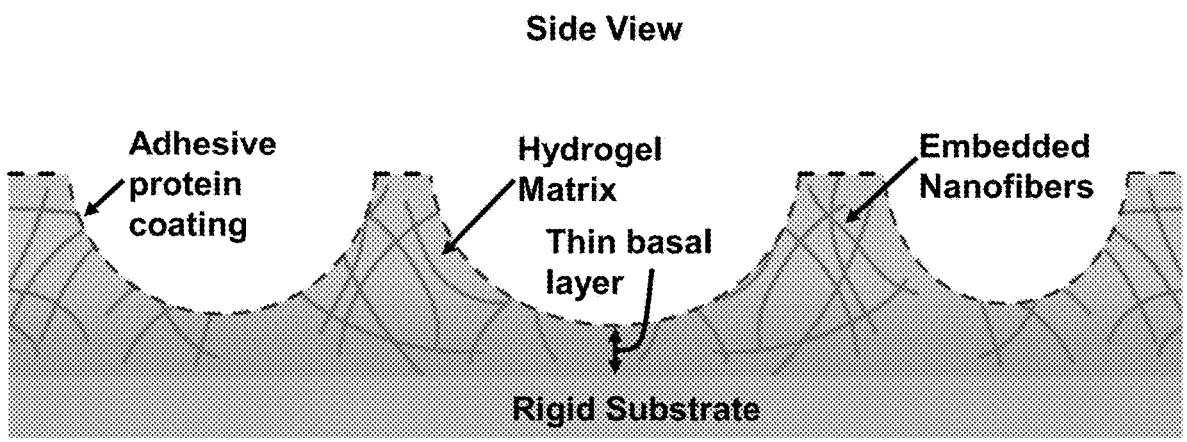

Computer-aided design (CAD) files were generated in SOLIDWORKS® consisting of an array of circles of 12, 15, and 18 µm diameters and used to generate the photomask pattern, as shown in FIG. 3. The design was chosen such that the distance between any two consecutive wells varied from 2 µm to 15 µm.

Micropatterned silicon wafers were obtained from the Utah Nanofab core lab at the University of Utah, USA, and standard contact lithography techniques were utilized to generate PDMS CellWell stamps. PDMS stamps were sterilized in an autoclave at 121° C. for 23 minutes. "Containment chambers" were microfabricated with 15 µm-tall walls, in which the CellWell casting process took place. These walls were thus constructed to be ~8 µm taller than the hemispheroids in the stamps to provide room for several microns of material to separate the basal surface of the cells from the underlying cover glass without adding excessive bulk that can confound imaging experiments conducted on standard inverted microscopes.

Agarose hydrogels (5% w/v) were prepared with slight modifications to the method described by H. M. Pauly et al. (*Biomacromolecules* 2017, 18 (7), 2220-2229). Poly(vinyl alcohol) (PVA) (15% w/v) hydrogels were prepared based upon the method described by S. Jiang et al. (*Mech Behav Biomed Mater* 2011, 4 (7), 1228-33)

PVA solution was prepared based upon the method described by A. G. Destaye et al. (*ACS Appl Mater Interfaces* 2013, 5 (11), 4745-52), and the electrospun nanofibers were obtained using the setup described by S. Mishra et al. (*J. Nanomater* 2012, 902491). PVA nanofibers were electrospun using an injection rate of 100 μL/h and an electric potential of 5 kV. The electrospun nanofibers were then crosslinked under via glutaraldehyde vapors for 48 hours in a vacuum desiccator. In this way, it is possible to consistently produce fibers with diameters closely matching those of ankle articular cartilage. After crosslinking, fibers may be manually chopped to reduce length for use in the nanocomposite casting process.

To cast CellWells, molten agarose solution, mixed with finely chopped crosslinked PVA nanofibers, was poured into a containment chamber, and the composite molten solution was stamped with a PDMS stamp at 4° C. for 6 mins. The stamp was then removed, revealing the bare CellWell. CellWells were then immediately hydrated with PBS-1× solution, UV sterilized for 30 mins, and coated with 10 μg/ml each of purified human plasma fibronectin and human placenta collagen type VI (Rockland Immunochemical) for 30 minutes at 37° C. For polydopamine (PDA)-functionalized samples, agarose was coated with 2 mg/mL dopamine-HCl (10 mM Tris Buffer, pH 8.5, 24 hours) at room temperature followed by coating with 25 μg/mL fibronectin for 24 hours at 37° C.

Figure 4A:
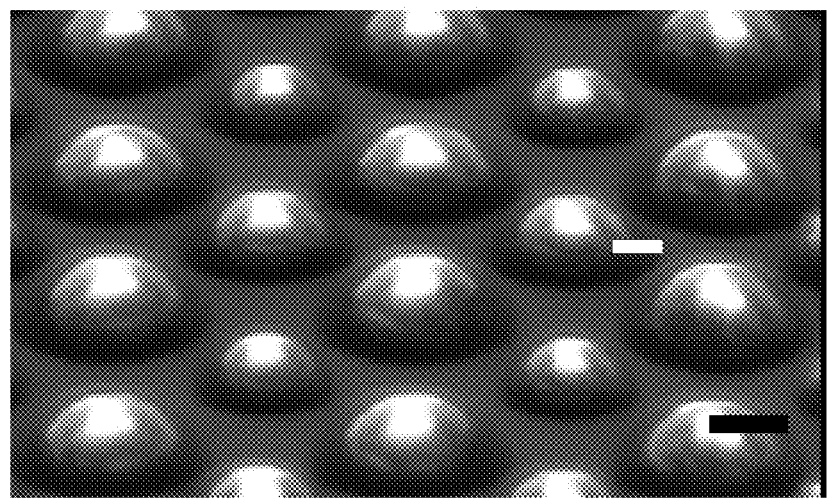
FIGS. 4A-D show that micropatterned wells match chondrocyte diameters.
Figure 4B:
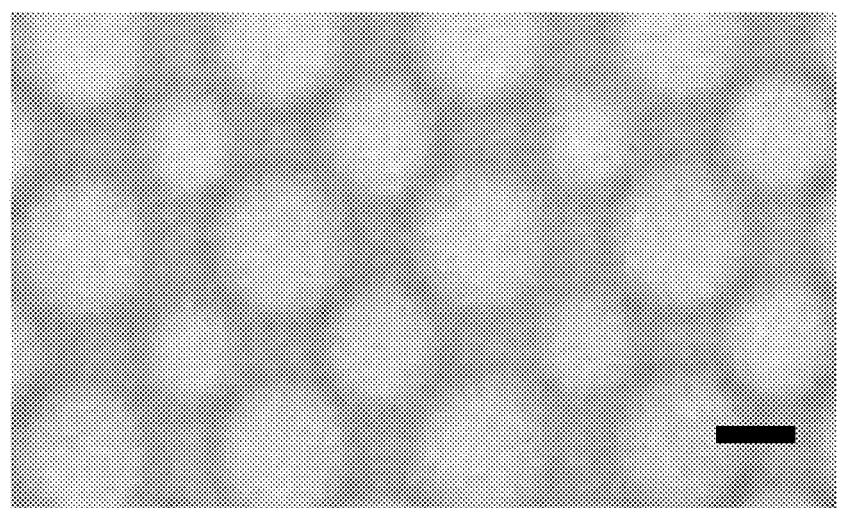
Figure 4C:
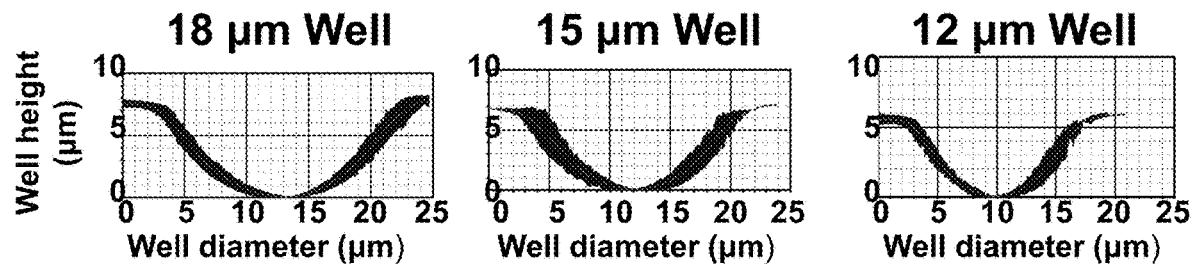
Figure 4D:
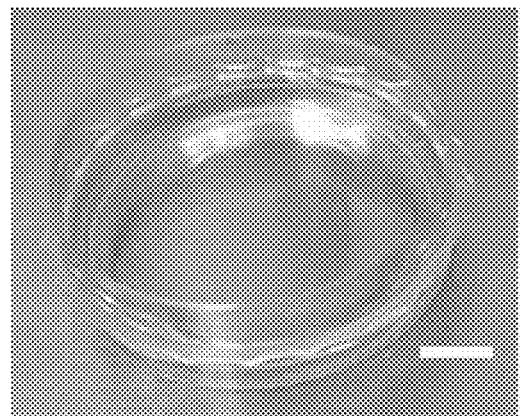

A Keyence VK-X250 optical profilometer was used to measure the dimensions of CellWell features (N=10). One of the limitations of our profilometer was that it could only work with dry samples and so we expected shrinkage effects in our CellWells due to the fact that the gelation mechanism of agarose is solely based on the physical hydrogen-bond networks. Thus, to ensure the fidelity of collected data, CellWells for these measurements were made out of PVA because PVA was made by freeze-thaw method, and frozen samples were able to be utilized to minimize the loss of feature height due to hydrogel drying compared to CellWells made of agarose. FIG. 4A shows scanning electron microscopy (SEM) images of the lithographic patterns on silicon that were used to create CellWell stamps. FIG. 4B shows a phase-contrast image of a CellWell with three sizes of wells precisely sized to fit individual articular chondrocytes. FIG. 4C shows the cross-sectional profiles of individual wells as measured by optical profilometry. Although frozen PVA CellWells were observed to have a decrease in well height by 7-15% due to imaging in the dried state, it can be easily seen in FIG. 4C that the geometry of the wells is hemispheroidal. The macro appearance of the CellWell is shown in FIG. 4D.

Example 4: Mechanical Characterization

Figure 5A:
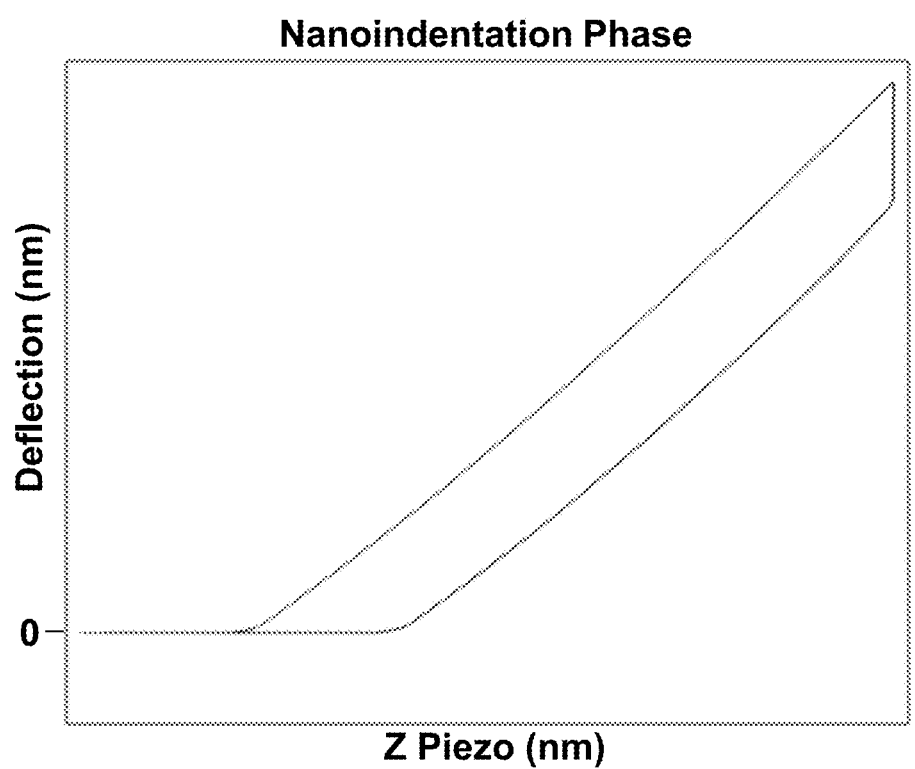
FIGS. 5A-B show AFM Experimental Design Schematics.
Figure 5B:
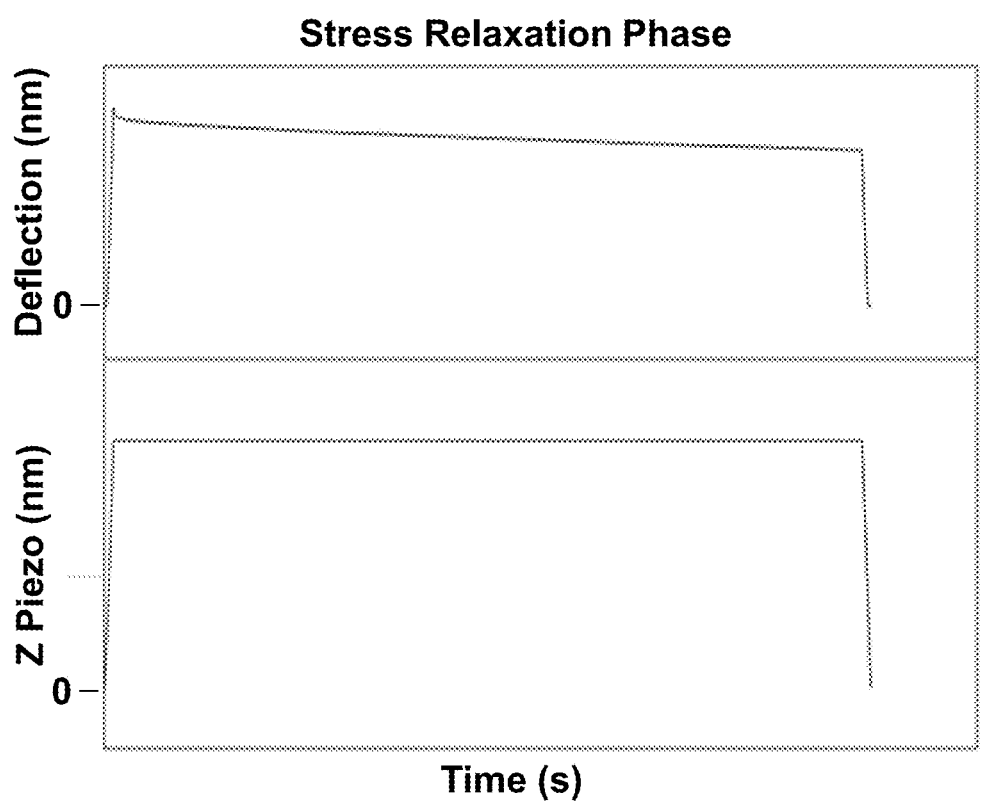

The viscoelastic properties of CellWells and articular cartilage were analyzed using an Asylum Research MFP-3D™ Atomic Force Microscope (AFM), with Igor Pro v6.37. Borosilicate glass spheres (4.8±0.3 μm diameter; SPI Supplies) were attached to the tip of AFM cantilevers (force constant in the range 0.04-0.7 N/m; All-In-One-Al-Tipless, Budget Sensors) using epoxy, and spring constants for each cantilever were determined thermally before experimentation. Stress relaxation of Agarose CellWells (N=3) and articular cartilage explants (N=3) was performed using a 5 μm/s approach velocity and 60 s relaxation time, as depicted in FIG. 5. The indentation phase was utilized for all elastic parameter calculations, while the relaxation phase was utilized for all viscosity parameter calculations.

Once the raw curves were obtained, the raw deflection curves were converted to force curves using Hooke's Law;

$$F = kx \quad (1)$$

Where F is the force, x is the deflection of the cantilever, and k is the cantilever spring constant determined thermally. To analyze the viscoelastic properties, a modified version of the Standard Linear Solid (SLS) Model as described by E. M. Darling et al. (*Osteoarthritis and cartilage* 2006, 14 (6), 571-9) was used.

All the force fittings were done as per the method described by E. M. Darling et al., described by the following equations:

$$F = \frac{4E_Y}{3(1-v^2)} R^{1/2} \delta^{3/2} \quad (2)$$

$$F(t) = \frac{4E_Y}{3(1-v^2)} R^{1/2} \delta^{3/2} \left(1 + \frac{\tau_\sigma - \tau_\varepsilon}{\tau_\varepsilon} e^{-\left(\frac{t}{\tau_\varepsilon}\right)}\right) \quad (3)$$

$$k_1 = E_R \quad (4)$$

$$k_2 = E_R \frac{(\tau_\sigma - \tau_\varepsilon)}{\tau_\varepsilon} \quad (5)$$

$$\mu = E_R(\tau_\sigma - \tau_\varepsilon) \quad (6)$$

$$E_0 = E_R \left(1 + \frac{\tau_\sigma - \tau_\varepsilon}{\tau_\varepsilon}\right) \quad (7)$$

$$E_Y = 1.5 E_R \quad (8)$$

Where $E_Y$ is the Hertz Compressive Moduli, F is the applied force during indentation, v is the Poisson's ratio, R is the radius of the indenter (2.5 μm), F(t) is the force measured as a function of time during stress relaxation, $E_R$ is the SLS Relaxation Moduli, $\tau_\sigma$ is the relaxation time under constant load, $\tau_\varepsilon$ is the relaxation time under constant deformation, $k_1$ and $k_2$ are the Kelvin spring elements, μ is the apparent viscosity and $E_0$ is the instantaneous moduli.

Eq (2) fits the Hertz equation, and Eq (3) fits the Standard Linear Solid (SLS) Model. The Poisson's ratio of agarose and cartilage were both assumed to be 0.33, and calculations were performed based on measurements at 1,500 nm of indentation depth (10% compressive strain for CellWells). Agarose CellWells (N=3) were separately indented at 15 μm/s to allow for direct comparison of compressive moduli with that of human pericellular matrix published by E. M. Darling et al. (*Biophys J* 2010, 98 (12), 2848-56).

For this comparison, the compressive moduli were obtained using Eq (2) at 8% compressive strain. All the mechanical measurements were taken between the wells due to the curvature of the wells limiting the ability to take AFM measurements within wells. To assess the stiffness within wells, the modulus of agarose samples with a thickness corresponding to the thickness of the CellWell at the bottom of wells (7 μm) was measured. Agarose samples of 3 μm thickness were also assessed to confirm a lack of substrate effects.

Figure 6A:
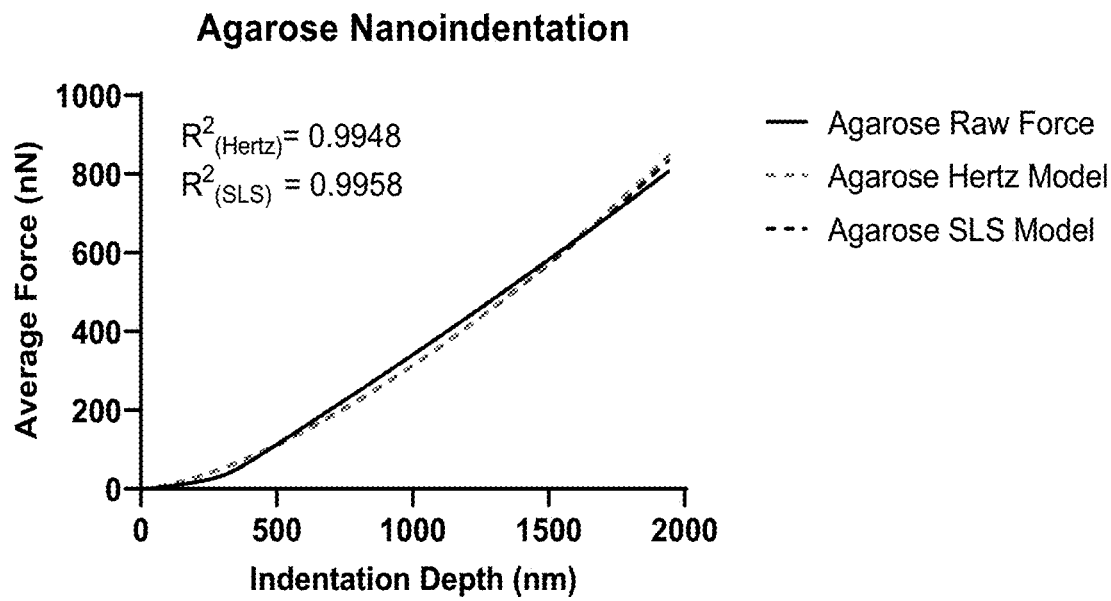
FIG. 6A-D show mechanical characterization of CellWell agarose and ankle articular cartilage.
Figure 6B:
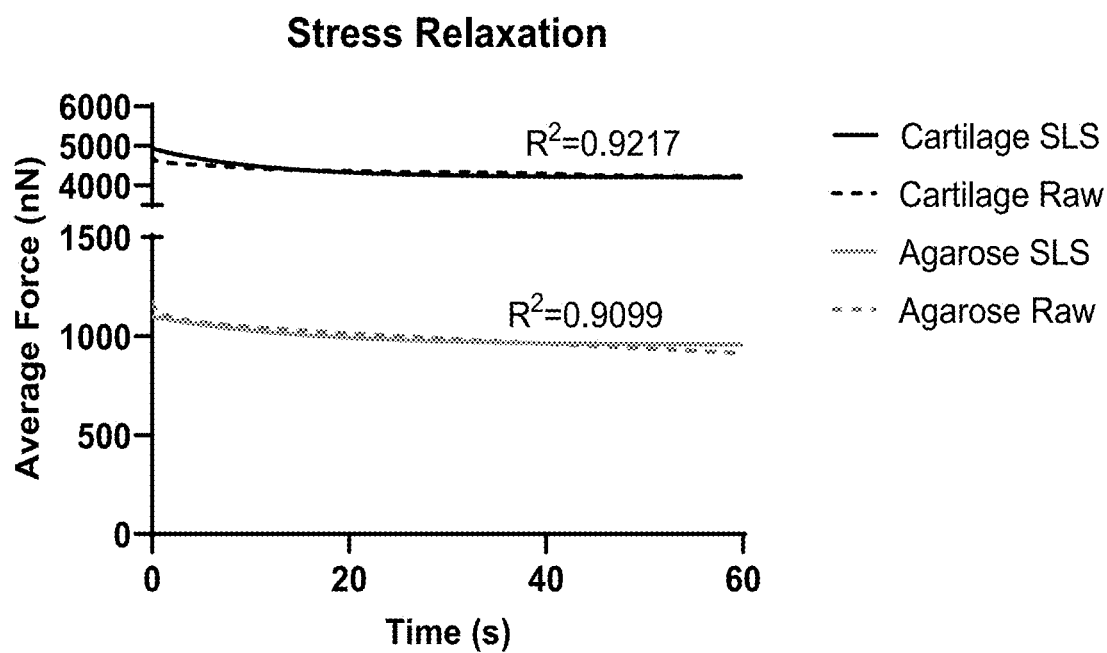
Figure 6C:
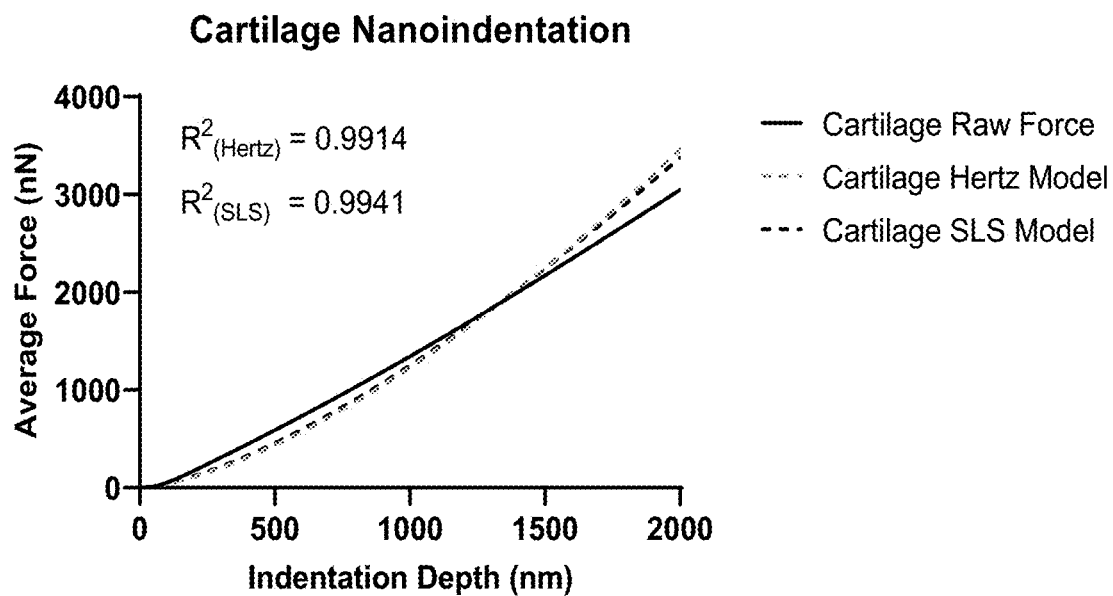

FIG. 6A and FIG. 6C depict average indentation curves at 5 μm/s for agarose and cartilage (N=3), respectively, along with both Hertzian (Eq (2)) and viscoelastic SLS model (Eq (3)) fits. FIG. 6B depicts average stress relaxation curves for agarose and cartilage along with the respective SLS fit for each based on Eq (3). These models were used to analyze the mechanical properties of agarose CellWells and ankle articular cartilage shown in Table 1.

FIG. 6 and Table 1 shows comparisons of the CellWell with human ankle articular cartilage. While slightly less stiff than cartilage as measured by AFM, the CellWell provides a much more comparable mechanical environment to the articular cartilage (70% lower) than commonly used tissue culture polystyrene ($10^4$ higher), coverglass ($10^5$ higher), or softer hydrogels ($10^2$ lower). Thus, the CellWell provides a much more appropriate mechanical environment for the cells than standard monolayer cultures.

TABLE 1

| Mechanical Parameter | CellWell (Mean ± S.D.) | Articular Cartilage (Mean ± S.D.) |
| --- | --- | --- |
| Hertz Elastic Modulus, $E_Y$ (kPa) | 144 ± 11.5 | 488 ± 102.5 |
| Relaxation Modulus, $E_R$ (kPa) | 95.8 ± 7.65 | 325 ± 68.3 |
| Instantaneous Modulus, $E_0$ (kPa) | 175 ± 24.5 | 575 ± 126.5 |
| $\tau_\sigma$ (s) | 17.3 ± 1.04 | 15.0 ± 4.80 |
| $\tau_\epsilon$ (s) | 14.3 ± 0.86 | 12.8 ± 4.09 |
| $k_1$ (kPa) | 95.8 ± 7.65 | 325 ± 68.3 |
| $k_2$ (kPa) | 20.8 ± 7.90 | 58.0 ± 16.8 |
| $\mu$ (kPa · s) | 296 ± 103.6 | 677 ± 60.9 |

Figure 6D:
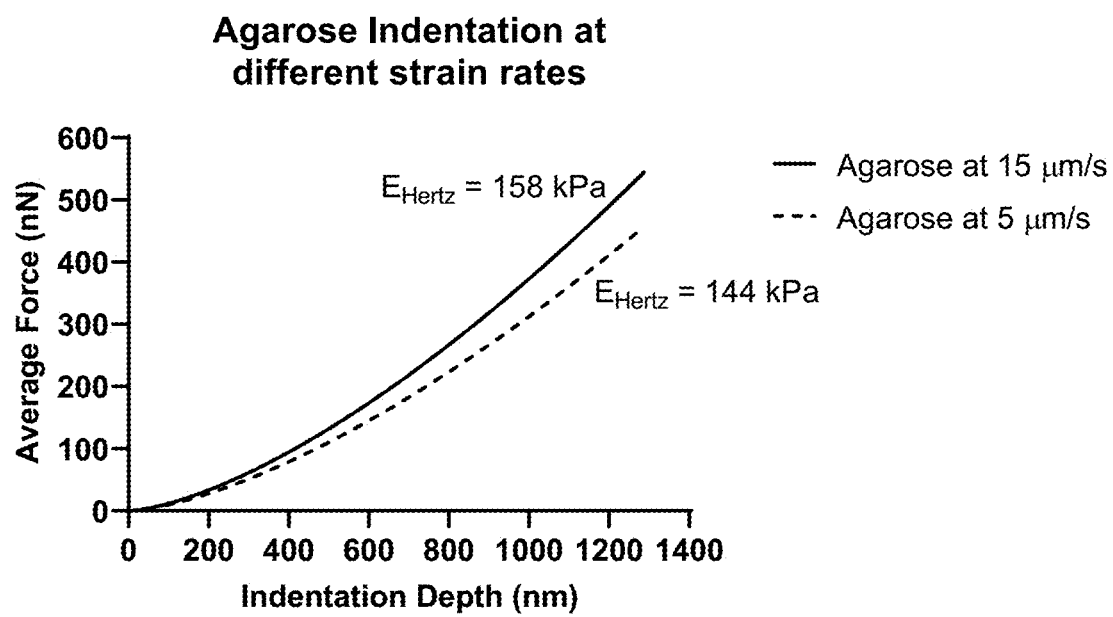

To compare the compressive mechanical properties of CellWells with that of human extracellular and pericellular matrices published by E. M. Darling et al., we indented the agarose CellWells at 15 µm/s. As a comparison, the agarose at 5 µm/s was also plotted to depict the effect of strain rate, as shown in FIG. 6D. Importantly, the CellWell elastic modulus of 158±0.6 kPa (S.D.) at 15 µm/s strain rate is very close to the reported, strain-rate matched, 162±22 kPa (S.D.) stiffness of knee cartilage PCM, indicating that it provides a highly appropriate mechanical environment for chondrocytes. Tables 2 shows the compressive stiffness of Agarose at different thicknesses. No substantial difference was observed between the stiffness of CellWells and agarose films of 7-µm and 3-µm stiffness, suggesting that the stiffness of the CellWell is homogeneous within and between wells, and that the thickness of the CellWell is sufficient to avoid substrate effects on the stiffness.

TABLE 2

| Substrate | Compressive Stiffness (Avg ± S.D.) (kPa) 15 µm/s indentation rate, 8% compressive strain |
| --- | --- |
| CellWell Inter-Well Areas (15 µm thickness) | 158.4 ± 0.6 |
| Agarose Film (7 µm thickness) | 160.6 ± 4.5 |
| Agarose Film (3 µm thickness) | 161.3 ± 1.0 |

Example 5: Optical Characterization

Optical transmittance of agarose, PVA nanofibers, and nanofiber-embedded CellWells (N=3 each) in the visible range was measured using a Video Spectral Comparator (VSC). Transmittance values were normalized against coverglass controls.

Figure 7:
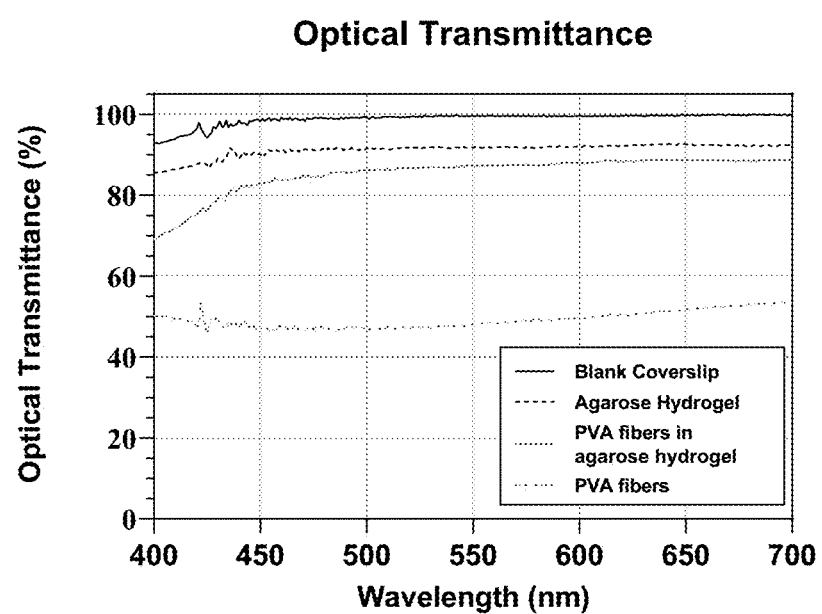
FIG. 7 shows optical transmittance of the CellWells measured using Video Spectral Comparator, confirming the optical transparency of the CellWells.

In general, the turbidity of 3D samples makes it difficult to image them beyond their surface level. To ensure that the CellWells are optically transparent enough to facilitate clear imaging on an inverted microscope with standard live-cell imaging techniques, we measured the optical transmittance of the CellWells across the visible range (FIG. 7). Even though the nanofibers had a transmittance of only about 50%, the transmittance of the hydrogels was found to be higher than 85%, and the nanofiber embedded hydrogels ranged from 70-85%.

Example 6: Protein Coating

Figure 8:
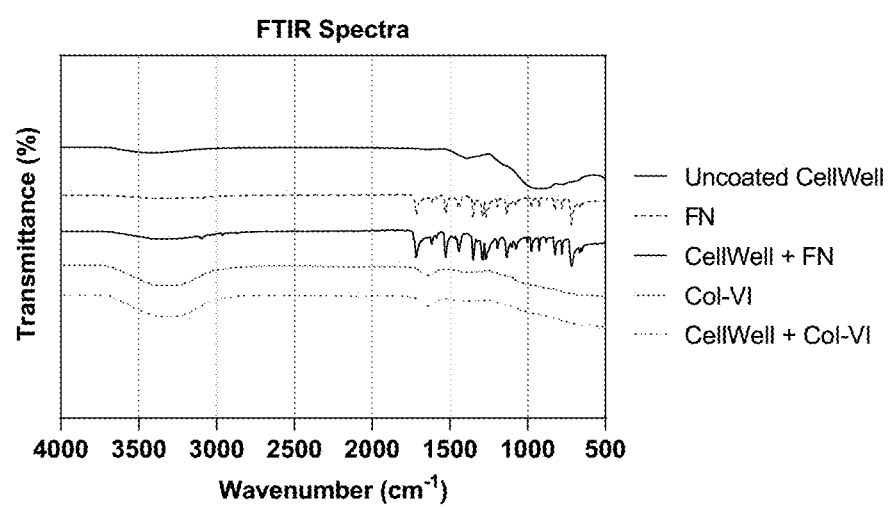
FIG. 8 shows successful coating of PCM proteins on the CellWells as confirmed by FTIR spectroscopy.

To confirm the adsorption of PCM proteins onto agarose CellWells, Fourier transform infrared spectra (FTIR) of coated CellWells were obtained for samples coated with either fibronectin (FN) or type-VI collagen (Col-VI). The FTIR spectra of an uncoated agarose CellWell and pure PCM proteins were also analyzed and used as controls. As depicted in FIG. 8, the FTIR spectra of agarose CellWells coated with FN or Col-VI was representative of the pure proteins, thus confirming that the PCM proteins were successfully adsorbed onto CellWells. However, a major limitation of this strategy is that the proteins do not adsorb strongly to agarose, which both limits initial cell adhesion and leads to a drastic loss of cell adhesion beyond 24-36 hours after seeding.

Example 7: Nanofiber Characterization

PVA and ankle cartilage collagen II nanofibers were imaged using a JEOL JEM-2100 $LaB_6$ transmission electron microscope (TEM), and diameters were measured using FIJI ImageJ v1.52n. PVA nanofibers were prepared and mounted on TEM grids for imaging. For collagen II diameter measurements, articular cartilage explants from the ankle were fixed with 2% PFA and 2.5% glutaraldehyde in 0.1 M cacodylate solution for 1 hour, followed by rinsing with sodium cacodylate buffer (0.1 M, pH 7.2) three times 5 min each. Then the tissues were postfixed with 0.5% $OsO_4$ and 0.5% potassium ferrocyanide for 30 min. After rinsing with cacodylate buffer, the tissues were dehydrated in a series of ethanol solutions (50%, 70%, 90% and 100% for 20 min each). The tissues were infiltrated with a mixture of ethanol and Araldite (2:1, 1:1, 1:2 ratios for 2 hours each) and cured with a fresh Araldite resin at 60° C. for 48 hr. Sections of 70 nm thickness were cut with an ultramicrotome (RMC Powertome XL), mounted on TEM grids, and stained with uranyl acetate and lead citrate.

Figure 9A:
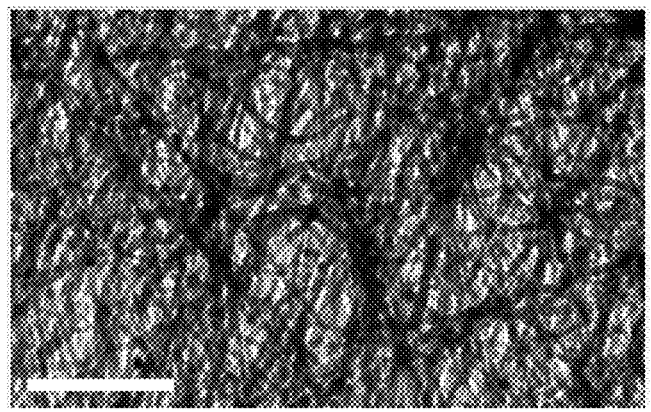
FIGS. 9A-C show electrospun PVA nanofibers have a diameter distribution representative of Collagen II fibers in ankle articular cartilage.
Figure 9A:
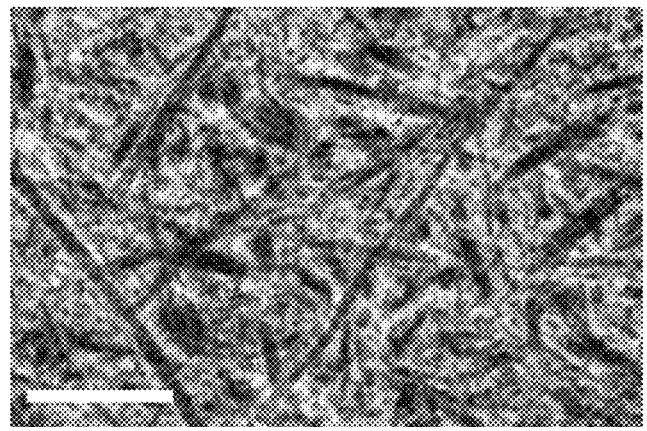
Figure 9B:
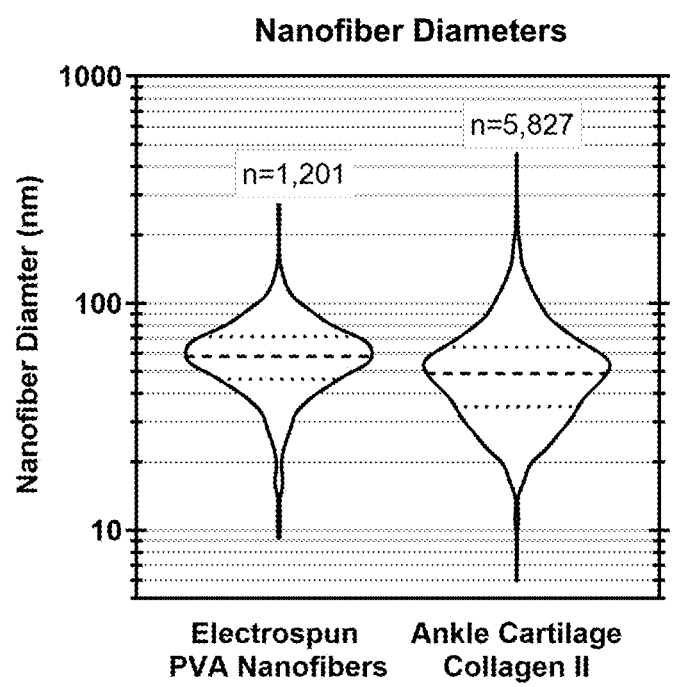
Figure 9C:
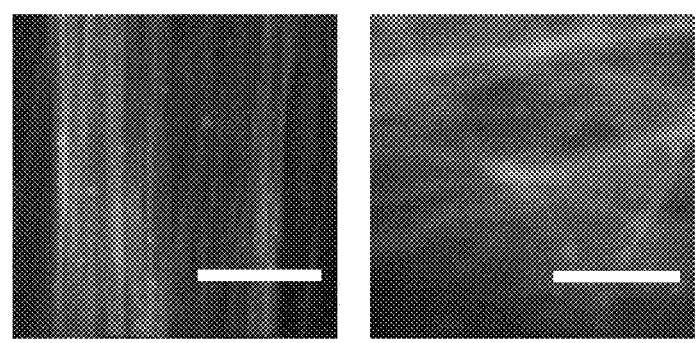

Since the nanofibers were embedded into the Agarose CellWells to model collagen II fibers within articular cartilage, it was essential to obtain the distribution of their diameters. To our knowledge, the diameters of collagen II nanofibers in ankle cartilage have never been reported; thus, their measurement was necessary here to optimize the conditions for electrospinning CellWell PVA nanofibers. FIG. 9A shows representative TEM images of both crosslinked PVA nanofibers and ankle articular cartilage, respectively. As seen in FIG. 9B, the collagen II nanofibers had a median diameter of 50 nm compared to the 60 nm median diameter of PVA nanofibers. The PVA nanofibers were found to be within 10 nm for the median as well as the $25^{th}$ and $75^{th}$ quartiles of the ankle collagen II nanofibers as well, substantiating the use of PVA nanofibers to model the collagen II nanofibers in the CellWell.

Example 8: Chondrocyte Viability and Morphology

Articular cartilage donors (N=4) had an age range of 42-77, a male/female ratio of 2/2, Collins scores ranging from 0-2, and no known history of OA. Primary human articular chondrocytes from de-identified ankle articular cartilage were isolated using sequential digestion with Pronase and collagenase, then plated in 35 mm tissue culture dishes and pre-incubated for 2 days to allow the cells to recover from the digestion process. Full-thickness articular cartilage explants were prepared before enzymatic digestion of the tissue using a 5 mm biopsy punch. Chondrocytes were gently lifted from the substrate using a 1-hour treatment with Pronase and collagenase and then seeded onto CellWells or control substrates. Chondrocytes were plated on top of tissue culture polystyrene or 15 μm-thick non-patterned agarose for 2D controls and encapsulated within thickness-matched agarose for 3D control samples. In all cases, chondrocytes were seeded with a density of $2 \times 10^5$ cells/cm$^2$. Culture media was replaced at one hour after initial seeding, after which cells were incubated continuously for 23 hours before imaging on an Olympus IX71 inverted epifluorescence microscope with a 20×, 0.46 N.A. objective (Olympus) and an Andor iXon Ultra EMCCD camera (Andor USA).

Figure 10:
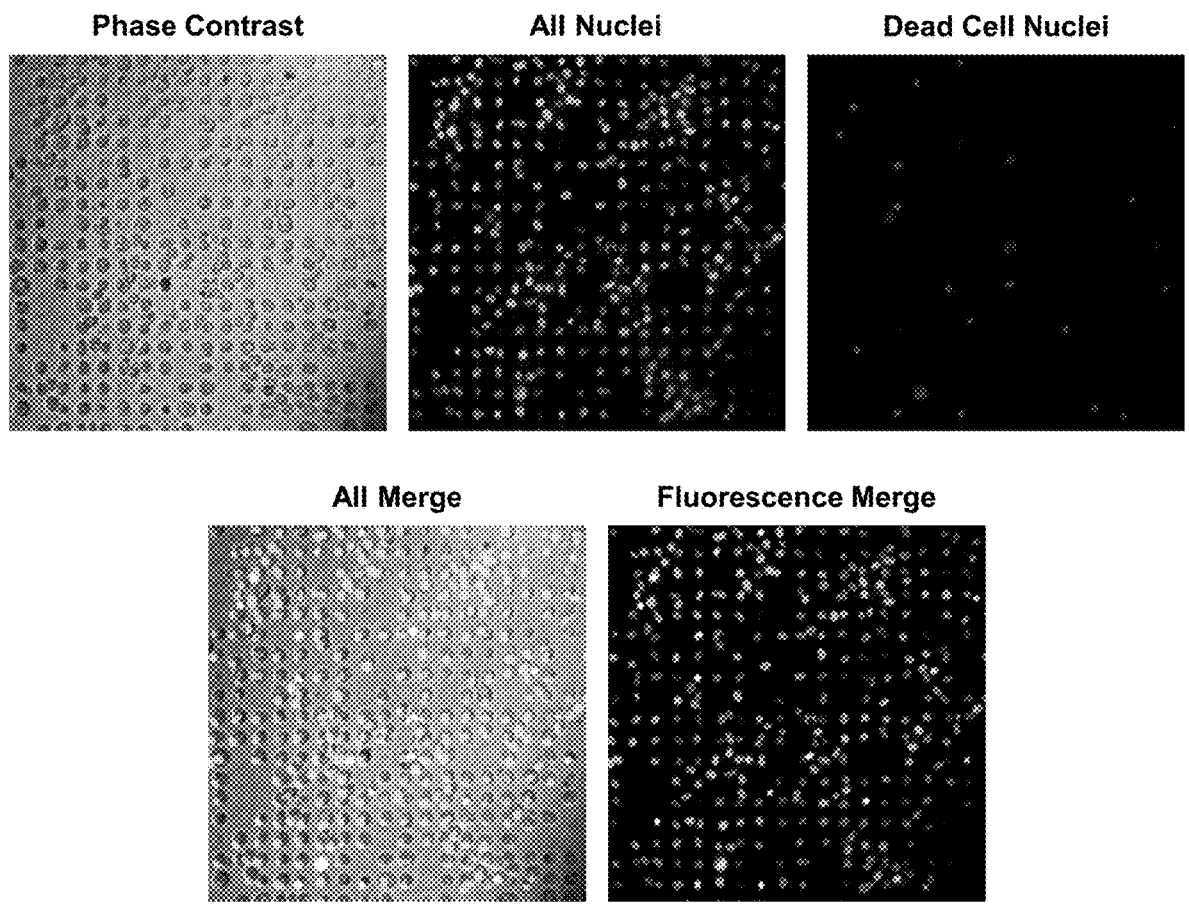
FIG. 10 shows chondrocyte viability is maintained in the CellWell. Chondrocyte viability of 85.6%±10.5% (S.D.) was observed at 24 hours using a standard inverted epifluorescence microscope. Cell-permeable NUCBLUE™ stains all nuclei, while cell-impermeable NUCGREEN™ stains only the nuclei of (dead) cells whose membranes have been disrupted. Scale bar 50 μm.

A fluorescent viability assay (ReadyProbes® Cell Viability Imaging Kit, ThermoFisher) was conducted to assess both the cytotoxicity of the CellWell and its compatibility for use with standard live-cell imaging techniques, as shown in FIG. 10. At 24-hours post-seeding, viability of 85.6%±10.5% (S.D.) was observed.

Figure 11:
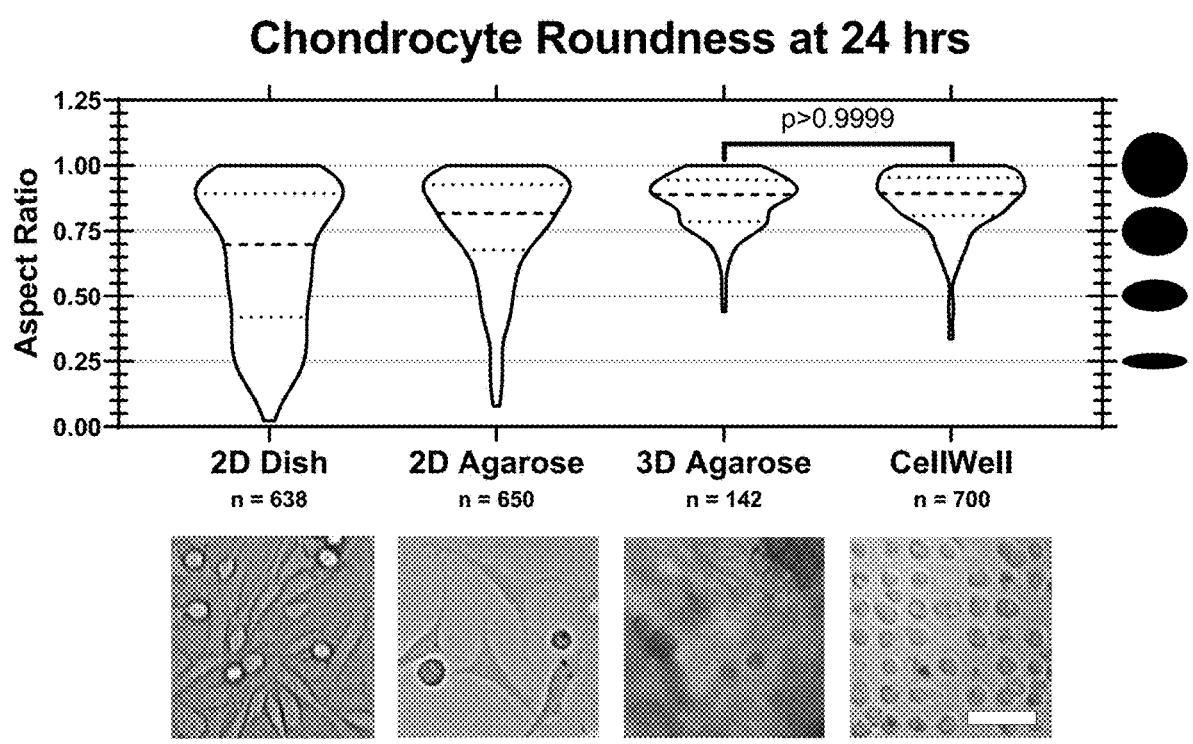
FIG. 11 shows CellWells promote maintenance of physiological chondrocyte morphology. Phase-contrast images of chondrocytes seeded using various platforms at 24 hours are shown below distributions of aspect ratios of chondrocytes seeded with each platform from n=3 donors. No difference was observed between 3D agarose and CellWell chondrocyte morphologies, indicating CellWell maintenance of physiological morphology, while all other samples were significantly different from each other (p≤0.0002) based on Kruskal-Wallis with Dunn's multiple comparisons post-hoc test. Scale bar 50 μm.
Figure 12:
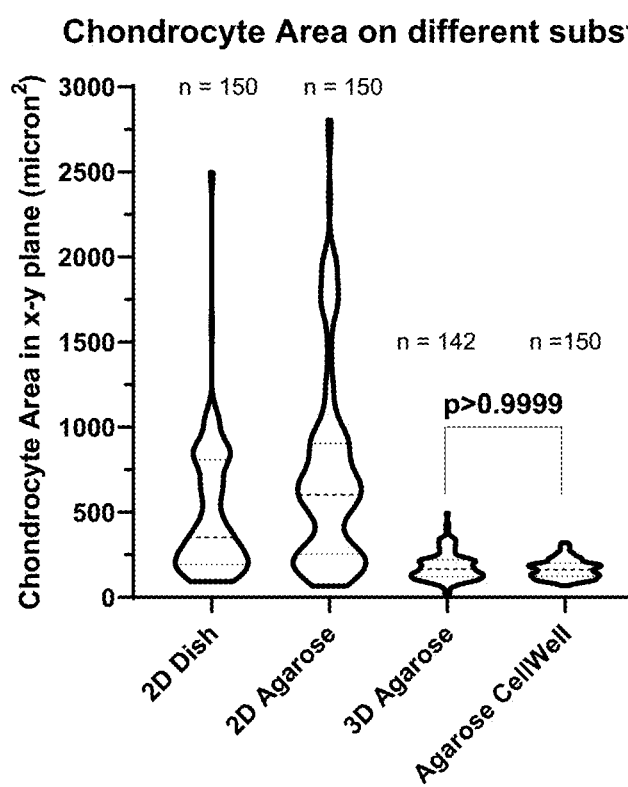
FIG. 12 shows distribution of chondrocyte XY area on the different platforms from n=3 donors. 3D agarose and CellWell chondrocyte areas were lower than chondrocytes plated on 2D substrates, indicating the 3D agarose and CellWell chondrocytes were taller along the Z axis than the cells on the 2D substrates. No difference was observed between 3D agarose and CellWell chondrocyte areas, while all other samples were significantly different from each other (p≤0.05) based on Kruskal-Wallis with Dunn's multiple comparisons post-hoc test.

As depicted in FIG. 11, we have found that the CellWell is highly effective at promoting a physiological rounded chondrocyte morphology at 24 hours of culture, as measured against standard 2D culture and 3D culture controls in which chondrocytes were embedded within agarose. FIG. 11 shows phase-contrast images and aspect ratios of chondrocytes seeded in agarose CellWells and control substrates—atop tissue culture polystyrene or agarose (2D culture) or encapsulated within agarose (3D culture). It can be easily seen that within 24 hours post-seeding, many chondrocytes in 2D culture had lost their canonical spheroid morphology and started to spread. On the other hand, the chondrocytes in CellWells maintained their canonical morphology similar to those in 3D agarose culture. No statistical difference was observed between 3D agarose and CellWell chondrocyte morphologies, indicating maintenance of physiological morphology by the CellWell, while all other samples were found to be significantly different from each other. To assess the height of cells in wells, cross-sectional measurements of the chondrocyte area on each substrate were obtained. As shown in FIG. 12, the area of the cells in CellWells closely matched the area of the cells in 3D encapsulated agarose, both of which were significantly lower, and therefore presumably taller, than the more spread cells plated on 2D controls.

All the images in FIGS. 10 and 11 were obtained using a standard inverted epifluorescence microscope. Contrary to some 2D micropatterned approaches, we do not have any non-adhesive areas to promote the cells being in a pattern. The geometry and spacing of our wells naturally promote the chondrocytes to fall into the wells.

Example 9: Long Term Chondrcoyte Morphology Maintenance

Figure 13A:
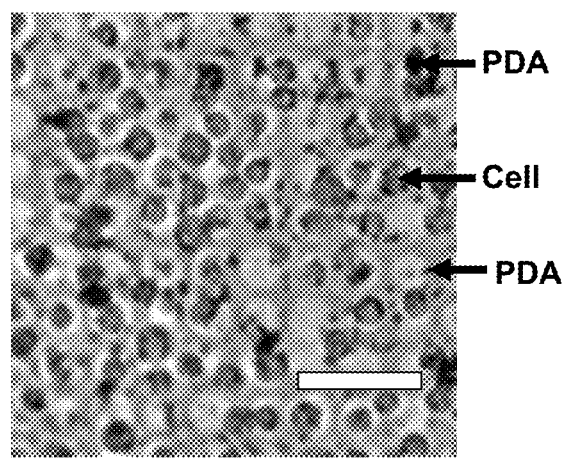
FIGS. 13A-C show polydopamine (PDA) functionalization promotes chondrocyte morphology maintenance in the CellWell for a 28-day period.
Figure 13B:
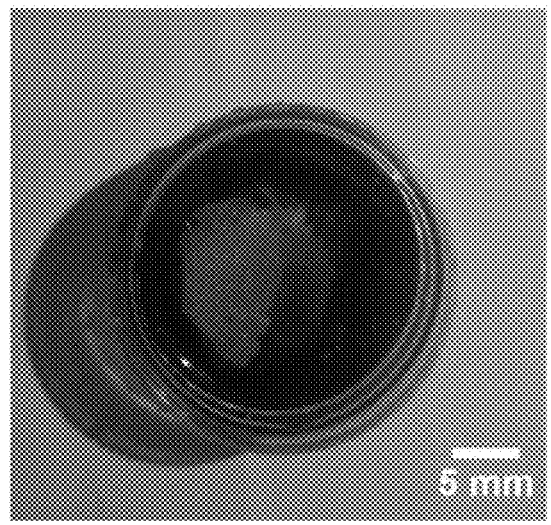
Figure 13C:
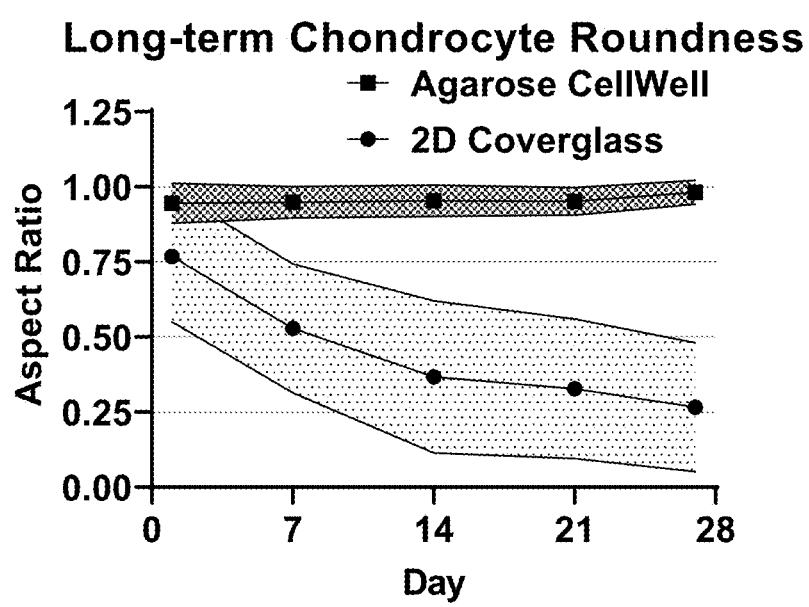

To achieve a long-term adherent culture, a strong surface chemistry is required to bind the PCM proteins onto the hydrogel surface. We found that a polydopamine (PDA)-based strategy can successfully maintain chondrocyte adherence for long-term culture up to 28 days, as shown in FIG. 13. This is a novel strategy that, to our knowledge, has never been used to modify the surface of agarose hydrogels. Previous micropatterning-based techniques designed to maintain the morphology of human chondrocytes have only been shown to be successful for a maximum of 7 days.

Figure 14:
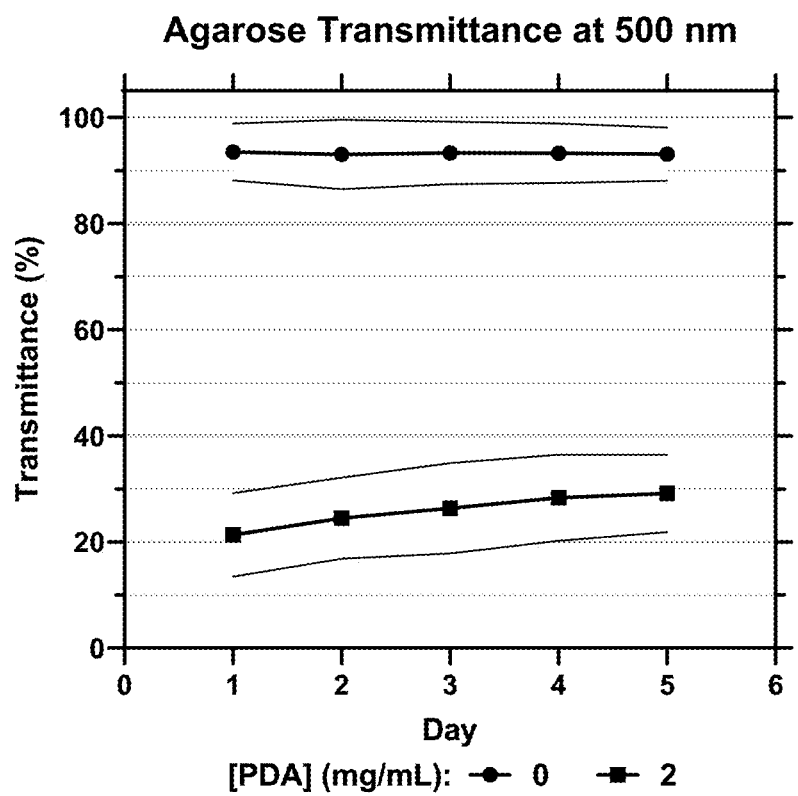
FIG. 14 shows the Transmittance at 500 nm of uncoated (0 mg/mL) and 2 mg/mL polydopamine (PDA) coated agarose (n=3 samples, mean±S.D.). Although the transmittance of PDA-coated agarose increased nearly 10% over five days, 2 mg/mL PDA lowered the transmittance enough to substantially hinder fluorescence imaging on PDA-functionalized CellWells.

A limitation of the current PDA-based functionalization strategy is the darkness of the polydopamine layer due to the concentration of PDA used (FIG. 14). For this initial study, 2 mg/mL PDA was utilized, as this is the most common concentration used across the literature. The PDA concentration may be further optimized to balance surface chemistry with optical transparency, thereby enabling the validation of phenotypic expression of phenotype marker proteins using immunofluorescence.

All publications and patent applications in this specification are indicative of the level of ordinary skill in the art to which this invention pertains. All publications and patent applications are herein incorporated by reference to the same extent as if each individual publication or patent application was specifically and individually indicated as incorporated by reference.

What is claimed is:

1. A composition comprising:
a hydrogel comprising embedded nanofibers, wherein the hydrogel is micropatterned with a plurality of wells, and wherein the plurality of wells is hemispheroidal in shape and has an average diameter of from about 5 μm to about 50 μm.

2. The composition of claim 1, wherein the hydrogel comprises a natural and/or synthetic polymer.

3. The composition of claim 1, wherein the hydrogel comprises agarose or polydimethyl siloxane.

4. The composition of claim 1, wherein the nanofibers are electrospun polyvinyl alcohol nanofibers.

5. The composition of claim 1, wherein the plurality of wells is separated by an inter-well spacing of from about 0.1 μm to about 30 μm.

6. The composition of claim 1, wherein the hydrogel is on a substrate.

7. The composition of claim 6, wherein the distance between the substrate and the bottom of the plurality of wells is from about 5 μm to about 100 μm.

8. The composition of claim 1, wherein the plurality of wells is seeded with cells at a cell seeding density of at least about 75,000 cells/cm$^2$, at least about 150,000 cells/cm$^2$, or at least about 275,000 cells/cm$^2$.

9. The composition of claim 8, wherein the cells comprise one or more of a chondrocyte cell, a stem cell, an adipose cell, and/or an immune cell.

10. The composition of claim 1, wherein the plurality of wells comprises a functionalized surface.

11. The composition of claim 10, wherein the functionalized surface comprises polydopamine.

12. A method of forming the composition of claim 1, the method comprising:
stamping a hydrogel comprising embedded nanofibers to form a plurality of wells in the hydrogel, wherein the plurality of wells is hemispheroidal in shape and has an average diameter of from about 5 μm to about 50 μm.

13. The method of claim 12, further comprising functionalizing the surface of the plurality of wells.

14. The method of claim 12, further comprising the step of mixing the hydrogel with the nanofibers before the stamping step.

15. A method of culturing cells, the method comprising:
providing the composition of claim 1;
seeding the plurality of wells with at least one cell per well.

16. The method of claim 15, wherein the plurality of wells is seeded with cells at a cell seeding density of at least about 75,000 cells/cm$^2$, at least about 150,000 cells/cm$^2$, or at least about 275,000 cells/cm$^2$.

17. The method of claim 15, wherein the plurality of wells comprises a polydopamine-based surface functionalization.

18. The method of claim 15, wherein the cells maintain adherence to the plurality of wells for at least about 28 days.

\* \* \* \* \*